(12) United States Patent
Thorson et al.

(10) Patent No.: US 8,232,254 B2
(45) Date of Patent: Jul. 31, 2012

(54) COLCHICINE NEOGLYCOSIDES AND METHODS FOR THEIR SYNTHESIS AND USE

(75) Inventors: Jon S. Thorson, Middleton, WI (US); Ahmed Aqeel, Herndon, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 362 days.

(21) Appl. No.: 11/868,737

(22) Filed: Oct. 8, 2007

(65) Prior Publication Data

US 2008/0171787 A1 Jul. 17, 2008

Related U.S. Application Data

(60) Provisional application No. 60/828,426, filed on Oct. 6, 2006.

(51) Int. Cl.
*A01N 43/04* (2006.01)
*A61K 31/70* (2006.01)
*C07H 21/00* (2006.01)
*C07H 19/00* (2006.01)
*C07H 5/04* (2006.01)
*C07H 5/06* (2006.01)
*C07H 1/00* (2006.01)
*C08B 37/00* (2006.01)

(52) U.S. Cl. .......... 514/42; 514/23; 536/22.1; 536/18.7; 536/1.11

(58) Field of Classification Search .............. 514/42, 514/23; 536/22.1, 18.7, 1.11
See application file for complete search history.

(56) References Cited

U.S. PATENT DOCUMENTS

| | | | |
|---|---|---|---|
| 4,160,452 | A | 7/1979 | Theeuwes |
| 4,256,108 | A | 3/1981 | Theeuwes |
| 4,265,874 | A | 5/1981 | Bonsen |
| 4,663,308 | A | 5/1987 | Saffran et al. |
| 4,777,049 | A | 10/1988 | Magruder et al. |

FOREIGN PATENT DOCUMENTS

| | | |
|---|---|---|
| EP | 0 647 450 A1 | 4/1995 |
| WO | 2004/111068 A1 | 12/2004 |

OTHER PUBLICATIONS

Ahmed, A., Peters, N. R., Fitzgerald, M.K., Thorson, J.S. (2006) MEDI-153: Glycorandomization of colchicine influences cytotoxicity and mechanism of action. Abstracts of Papers, 232$^{nd}$ American Chemical Society National Meeting, San Francisco, CA, Sep. 2006.*
Greene, T.W. and Wuts, P.G.M. (1991) Protective Groups in Organic Synthesis, published by John Wiley & Sons, Inc., p. 351-352.*
Hardy et al., Aliment. Pharmacol. Therap., 1987, 1, 273-280.
Langenhan et al., Proc. Natl. Acad. Sci., U.S.A, 2005, 102, 12305.
Thorson et al., Carbohydrate-Based Drug Discovery, 2003, 685.
Griffith et al., Curr. Opin. Biotech., 2005, 16, 622.
Zhang et al., Science, 2006, 313, 1291.
Fu et al., Nat. Biotech., 2003, 21, 1467.
Koyama et al, Biopharm. Drug Dispos., Dec. 1997, 791-801.
Bonne et al., J. Biol. Chem., 1985, 260, 2819.
Friend et al., J. Med. Chem., 1984, 27, 261-268.
Jordan et al., Nat. Rev. Cancer, 2004, 4, 253.
Aqeel Ahmed, et al., Colchicine Glycorandomization Influences Cytotoxicity and Mechanism of Action, J. Am. Chem. Soc., Oct. 13, 2006, pp. 14224-14225, vol. 128.
International Search Report corresponding to PCT/US2007/080696, under date of mailing of May 27, 2008.

* cited by examiner

*Primary Examiner* — Scarlett Goon
(74) *Attorney, Agent, or Firm* — Quarles & Brady LLP

(57) ABSTRACT

Colchicine neoglycosides, method for their synthesis and methods for their use are disclosed. The invention provides analogs of colchicine glycosylated to include a sugar moiety on a colchicine scaffold that is generally unglycosylated in nature. The colchicine neoglycosides disclosed herein are shown to have cytotoxic effects equivalent to at least the known cytotoxins paclitaxel and doxorubicin. Further, the neoglycosides disclosed according to the invention have physiologic effects not previously recognized in the alkaloid family that includes colchicine but recognized in other cytotoxic drug families such as the taxanes which act by stabilizing tubulin formation.

2 Claims, 12 Drawing Sheets

COLCHICINE NEOGLYCOSIDES AND METHODS FOR THEIR SYNTHESIS AND USE

CROSS-REFERENCE TO RELATED APPLICATIONS

This application claims the benefit of to U.S. Provisional Application No. 60/828,426, filed Oct. 6, 2006, the entirety of which is incorporated by reference herein.

STATEMENT RELATED TO FEDERAL FUNDING

This research was supported in part by National Institutes of Health Grants CA113297 and AI052218. The federal government has certain rights to this invention.

FIELD OF THE INVENTION

This invention is generally directed to colchicine analogs and more particularly to colchicines analogs produced by glycorandomization.

BACKGROUND OF THE INVENTION

Sugars appended to pharmaceutically important natural products are known to influence drug solubility, pharmacology, target recognition, toxicity and mechanism of action (Thorson, J. S.; Vogt, T. Carbohydrate-Based Drug Discovery 2003, 685. Wong C H. (Ed): Weinheim:Wiley-VCH). However, studies designed to systematically understand and exploit the role of carbohydrates in drug discovery are often limited by the availability of practical synthetic tools (Griffith, B. R., et al., Curr. Opin. Biotech. 2005, 16, 622). For instance, two complementary strategies that allow for the rapid glycosylation of natural product scaffolds have been reported. The first (chemoenzymatic glycorandomization) utilizes a set of flexible enzymes (an anomeric kinase, sugar-1-phosphate nucleotidylyltransferase and natural product glycosyltransferase), (Zhang, C. et al., Science 2006, 313, 1291) while the second (neoglycorandomization) employs a single reaction between a free reducing sugar and a methoxyamine-appended aglycon (Langenhan, J. M. et al., Proc. Natl. Acad. Sci. U.S.A. 2005, 102, 12305). While both methods have been successful in preparing a glycorandomized library and identifying compounds with notable activities (Fu, X., et al., Nat. Biotech. 2003, 21, 1467), applications of glycorandomization to date have been restricted to the natural positions of O-glycosylation within natural products.

Glycosylation of natural compounds alters their bioavailability and pharmacokinetics (Koyama, H. et al., Biopharm Drug Dispos. 1997 December; 18(9):791-801). Further, other studies have shown that glycosylation can be exploited to design recombinant drugs which optimize pharmacokinetics (Klgelberg, H., Glycobiology, 2006 Sep. 25). However, in these cases the glycosylated bioactive compounds had naturally occurring glycosylated derivatives.

Colchicine is one bioactive compound that does not have naturally occurring glycosylated derivatives. Colchicine is an alkaloid known as a treatment for gout, Bechet's disease and Mediterranean fever as well as for its cathartic and emetic effects. Colchicine is also thought to have efficacy as a treatment for cancer. Unfortunately, colchicine's effectiveness as a therapeutic is limited by its toxicity as high doses can result in death from respiratory failure.

In the search for a wider spectrum of antibiotics and therapeutics, the present invention provides a method to synthesize and identify glycosylated derivatives or analogs of naturally occurring bioactive compounds there are not normally glycosylated in nature. Thus, the bioactivity and pharmacokinetics of such compounds could be altered to provide new classes of compounds with hitherto unidentified actions and/or actions that are hybrid between the non-glycosylated base and the carbohydrate moiety that is conjugated thereto.

SUMMARY OF THE INVENTION

Colchicine neoglycosides, methods for their synthesis and methods for their use are disclosed. The invention provides analogs of colchicine glycosylated to include a sugar moiety on a colchicine scaffold that is generally unglycosylated in nature. The colchicine neoglycosides disclosed herein are shown to have cytotoxic effects equivalent to at least the known cytotoxins paclitaxel and doxorubicin. Further, the neoglycosides disclosed according to the invention have physiologic effects not previously recognized in the alkaloid family that includes colchicine but recognized in other cytotoxic drug families such as the taxanes which act by stabilizing tubulin formation. Thus, the neoglycosides disclosed herein represent new compounds not previously recognized to have therapeutic effects.

In one preferred embodiment, the invention includes a colchicine neoglycoside having the structure:

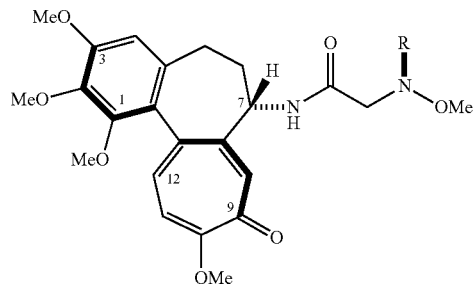

wherein R is:

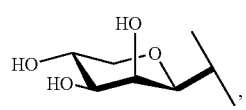

Col1

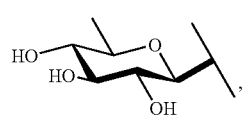

Col2

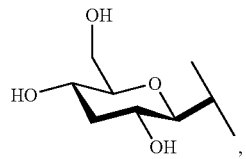

Col3

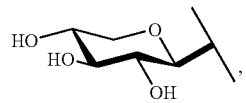

Col4

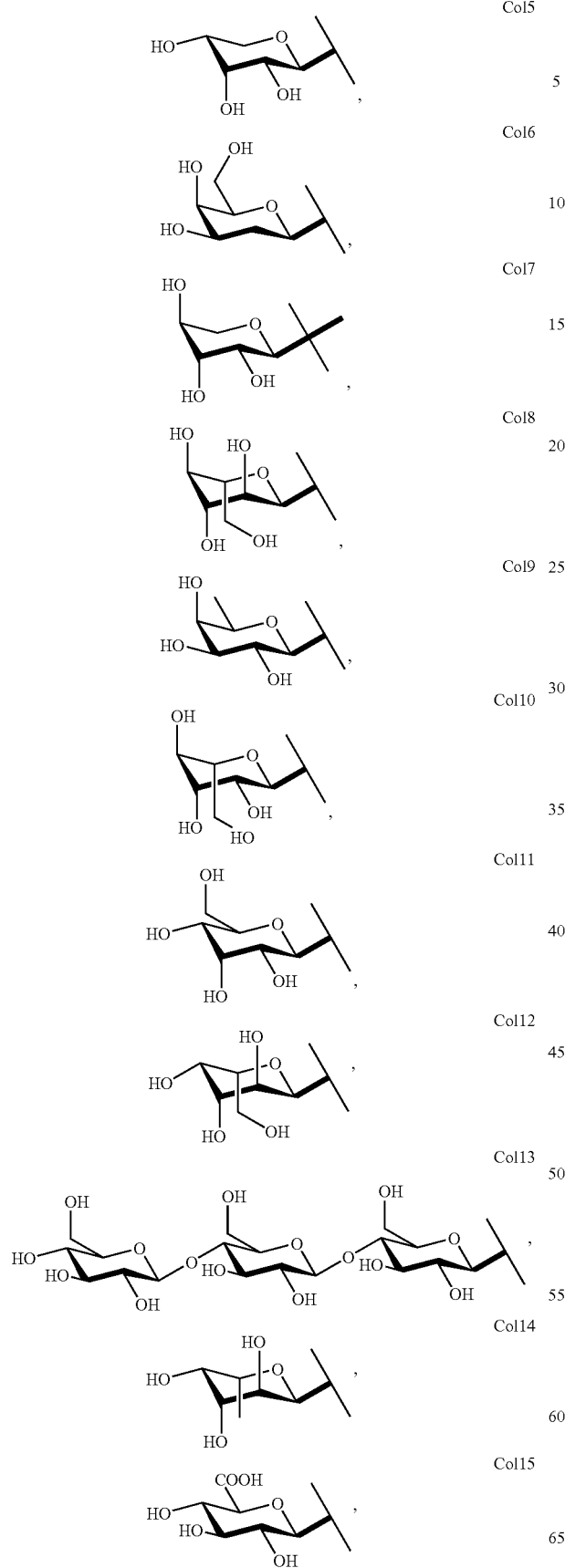
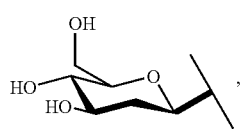
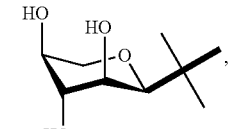
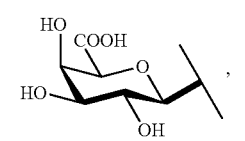
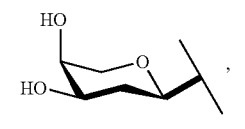
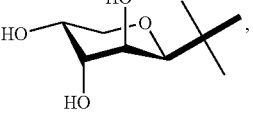
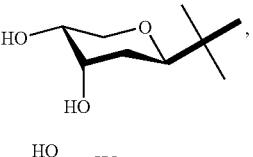
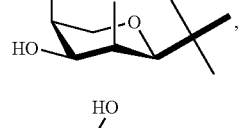
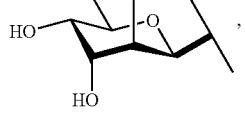
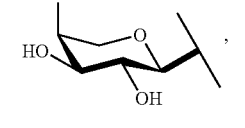
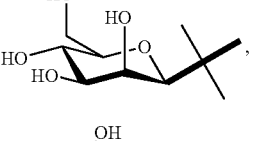
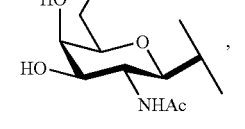
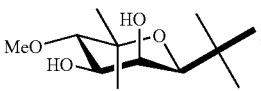

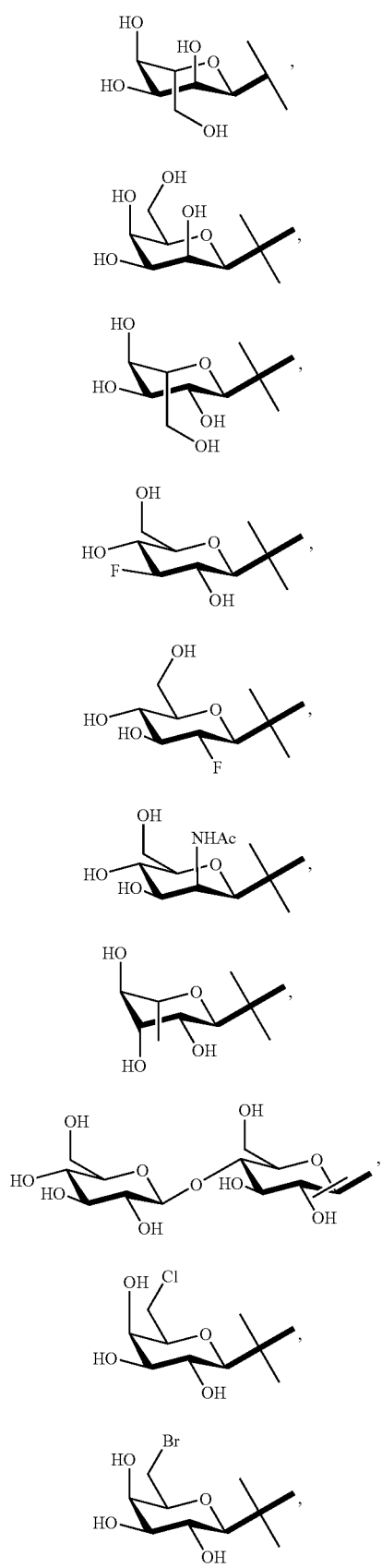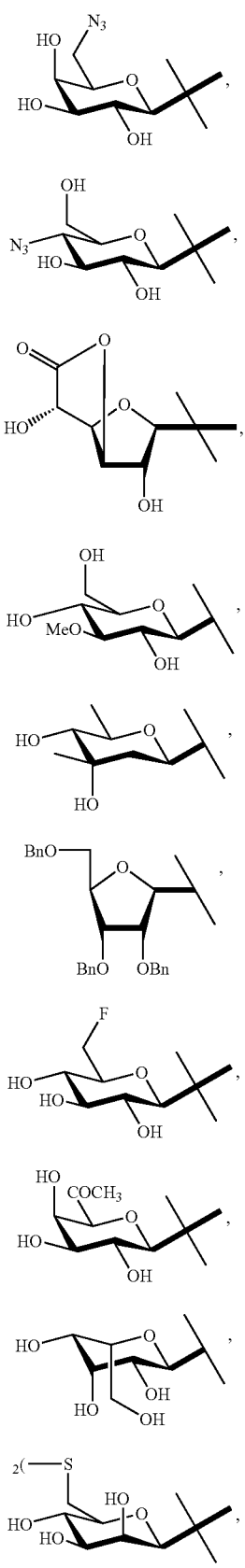

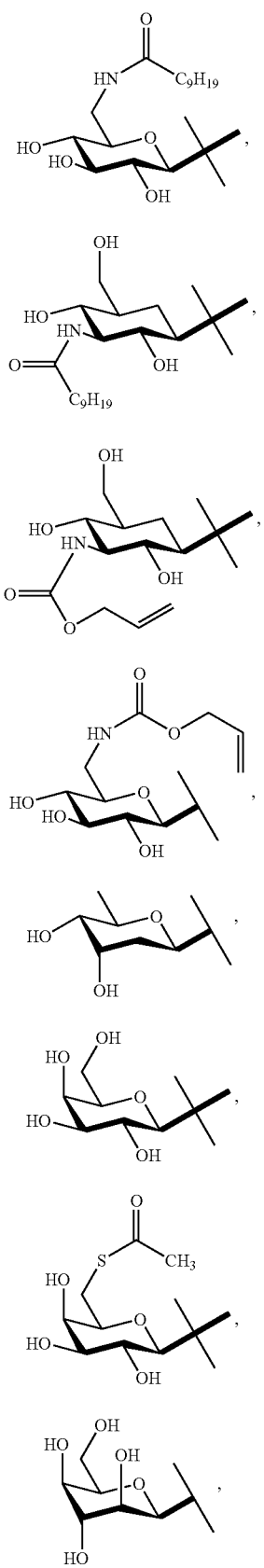
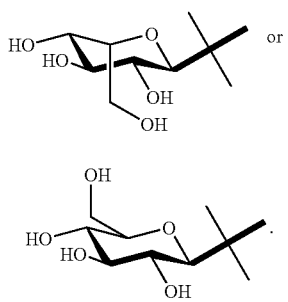
In particularly preferred embodiments, the colchicine neoglycoside has the
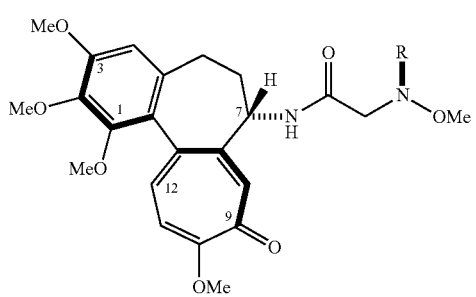
wherein R is:
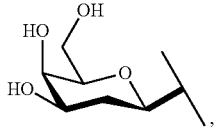
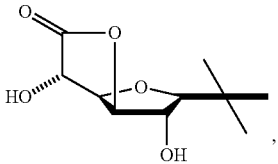
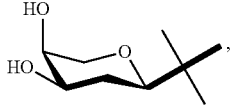
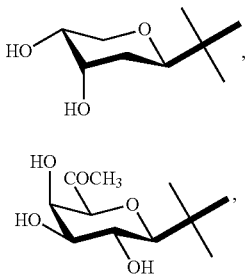

-continued

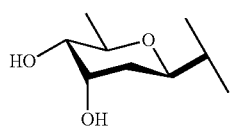 Col65

In another embodiment, the invention comprises an intermediate in the synthesis of colchicines neoglycosides, namely, a methoxyamine-appended colchicine according to the structure:

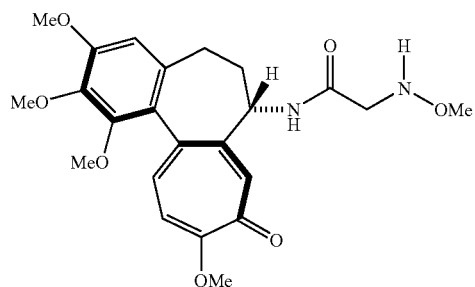

In yet another embodiment, the invention includes a method of synthesizing a colchicine neoglycoside according to the reaction:

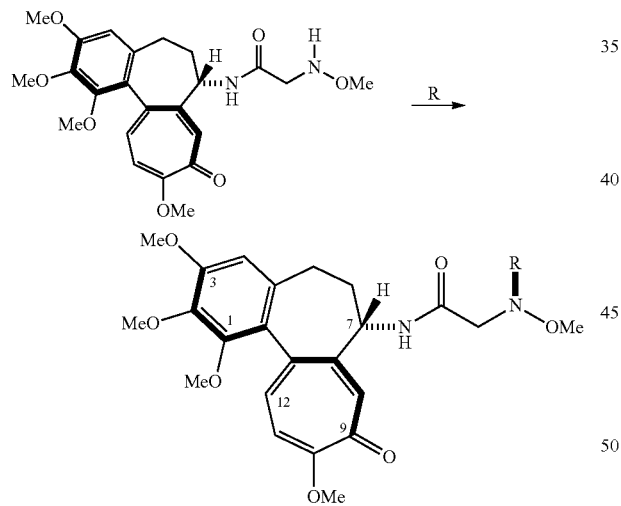

wherein R is:

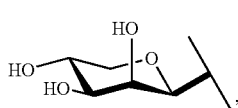 Col1

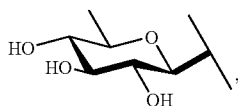 Col2

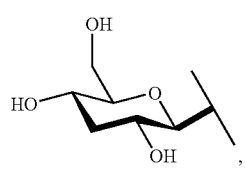 Col3

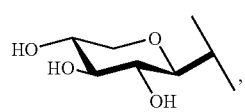 Col4

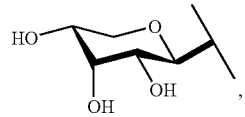 Col5

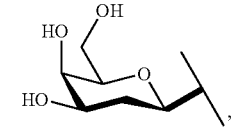 Col6

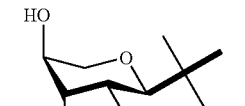 Col7

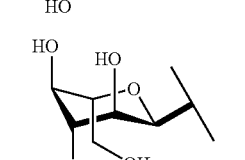 Col8

 Col9

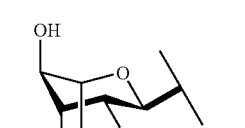 Col10

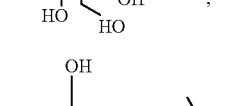 Col11

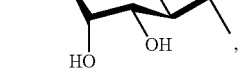 Col12

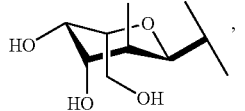 Col13

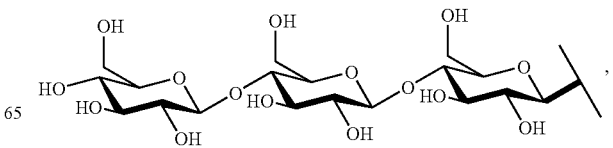

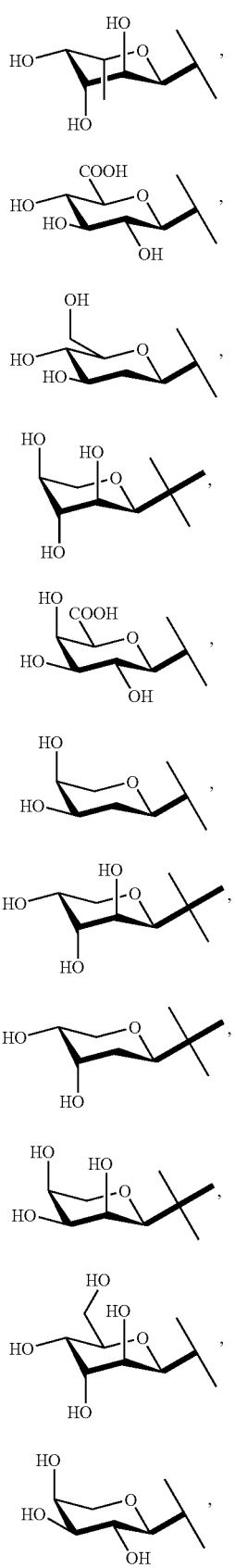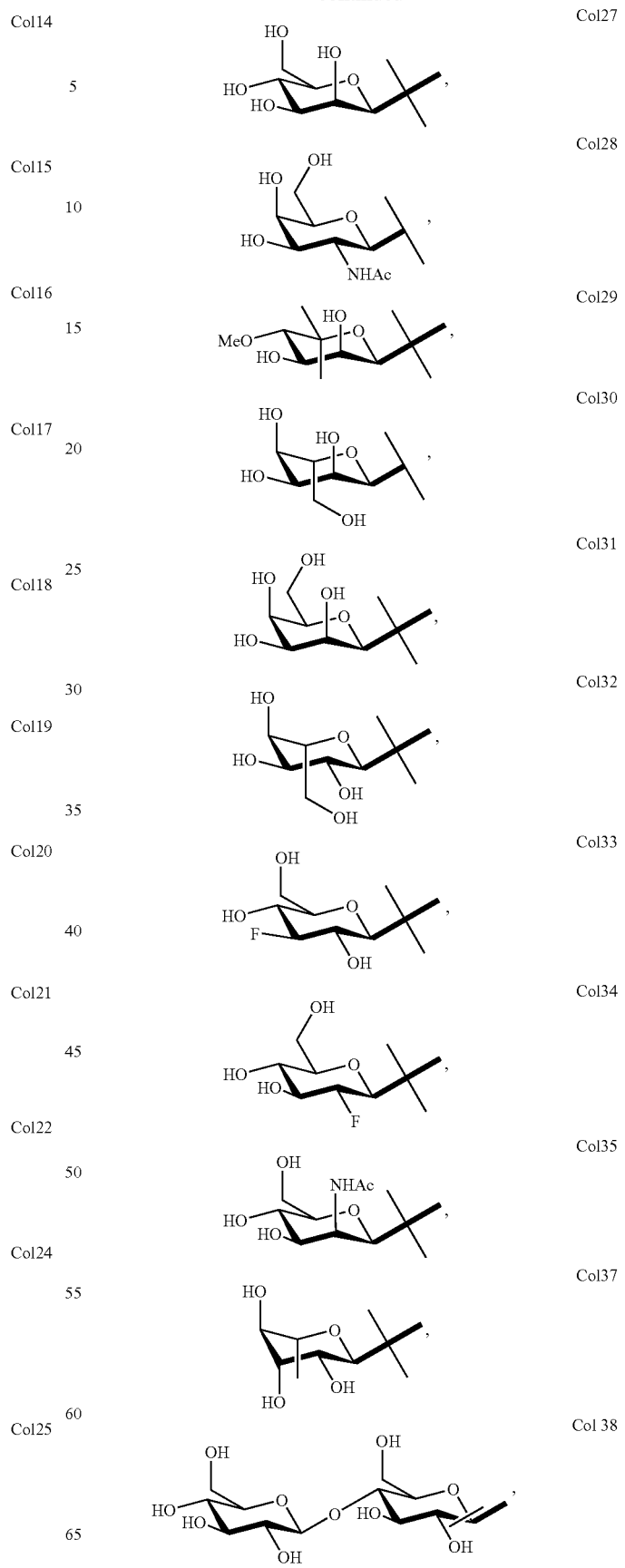

-continued

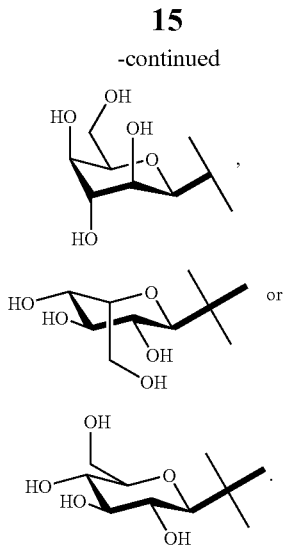

In some exemplary embodiments the reaction is carried out at 40° C. in the presence of 3:1 DMF/AcOH.

In another exemplary embodiment, the invention provides a method of treating cancer, arthritis, Mediterranean fever, amyloidosis, scleroderma, irritable bowel syndrome or gout comprising administering to a patient in need thereof a therapeutic amount of a colchicine neoglycoside in combination with other therapeutically effective drugs.

In some preferred embodiments, the other therapeutically effective drugs are selected from an alkaloid, an anthracycline, a taxane and combinations thereof.

These and other features of various exemplary embodiments of the methods according to this invention are described in, or are apparent from, the following detailed description of various exemplary embodiments of the methods and compositions according to this invention.

BRIEF DESCRIPTION OF THE FIGURES

Various exemplary embodiments of the methods of this invention will be described in detail, with reference to the following figures, wherein.

DETAILED DESCRIPTION OF THE INVENTION

Figure 1:
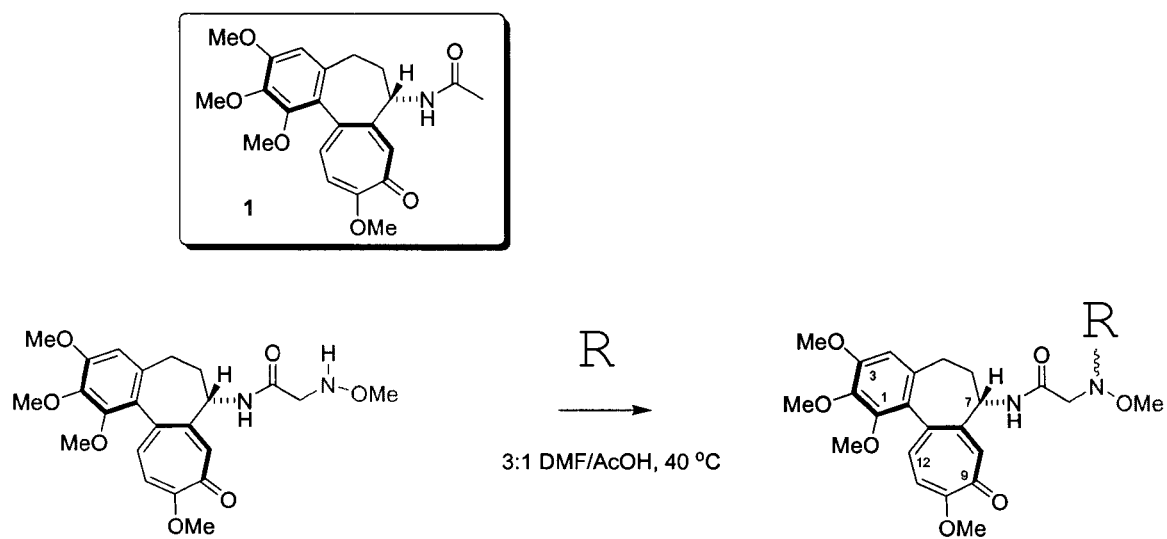
FIG. 1 shows the reaction by which neoglycosylation toward amine-bearing scaffolds and the potential benefit of glycosylating non-glycosylated natural products is achieved.

A colchicine neoglycoside library and methods for its synthesis is disclosed. The invention provides analogs of colchicine glycosylated to include a sugar moiety on a colchicine scaffold that is generally unglycosylated in nature. The colchicine neoglycosides disclosed herein are shown to have cytotoxic effects equivalent to at least the known cytotoxins paclitaxel and doxorubicin. Further, the neoglycosides disclosed according to the invention have physiologic effects not previously recognized in the alkaloid family that includes colchicine but recognized in other cytotoxic drug families such as the taxanes which act by stabilizing tubulin formation. Thus, the neoglycosides disclosed herein represent new compounds not previously recognized to have therapeutic effects.

In one preferred embodiment, the invention includes a colchicine neoglycoside having the structure:

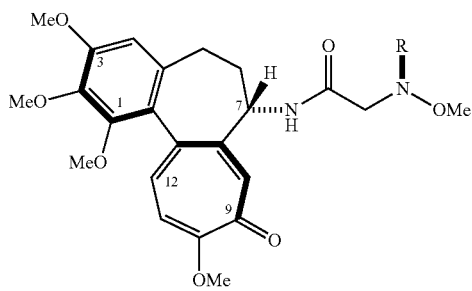

wherein R is:

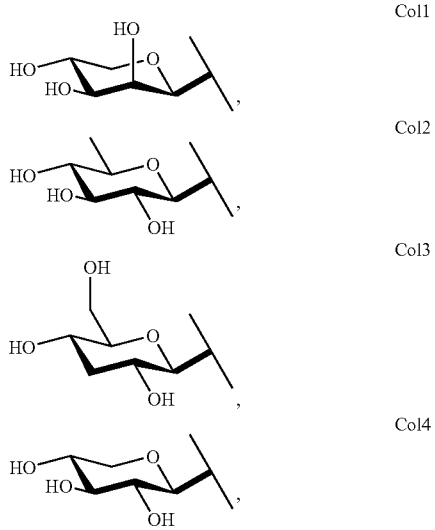

-continued
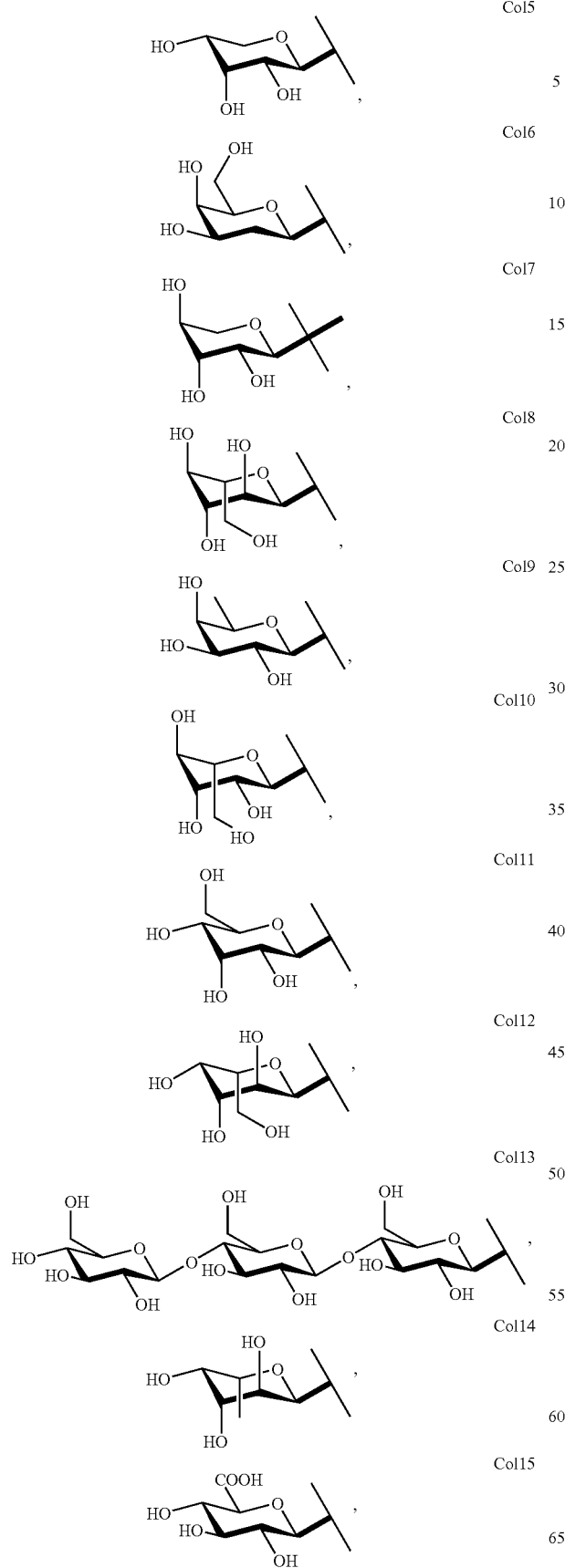
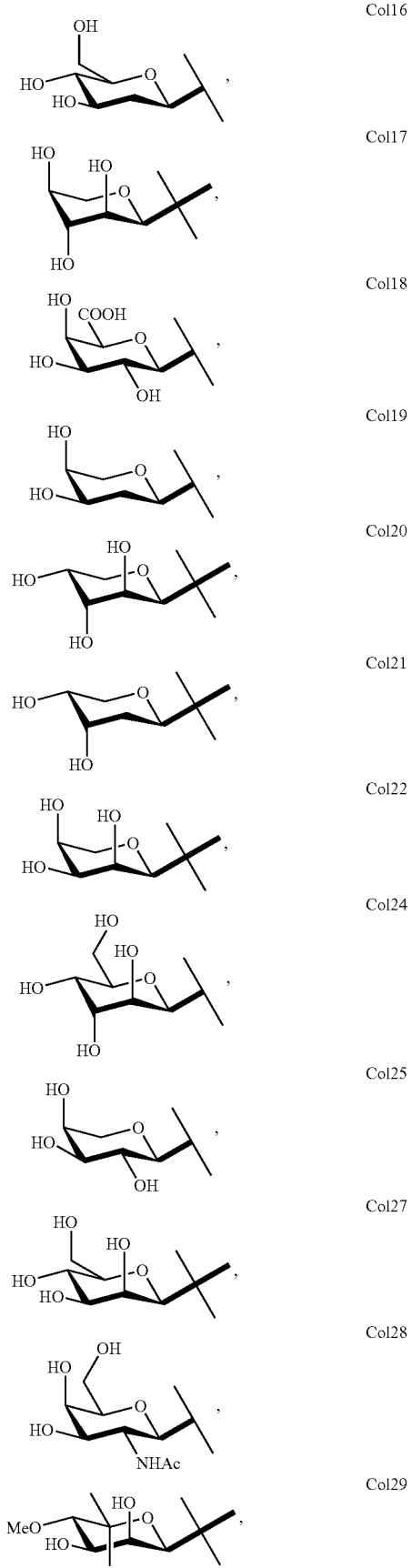

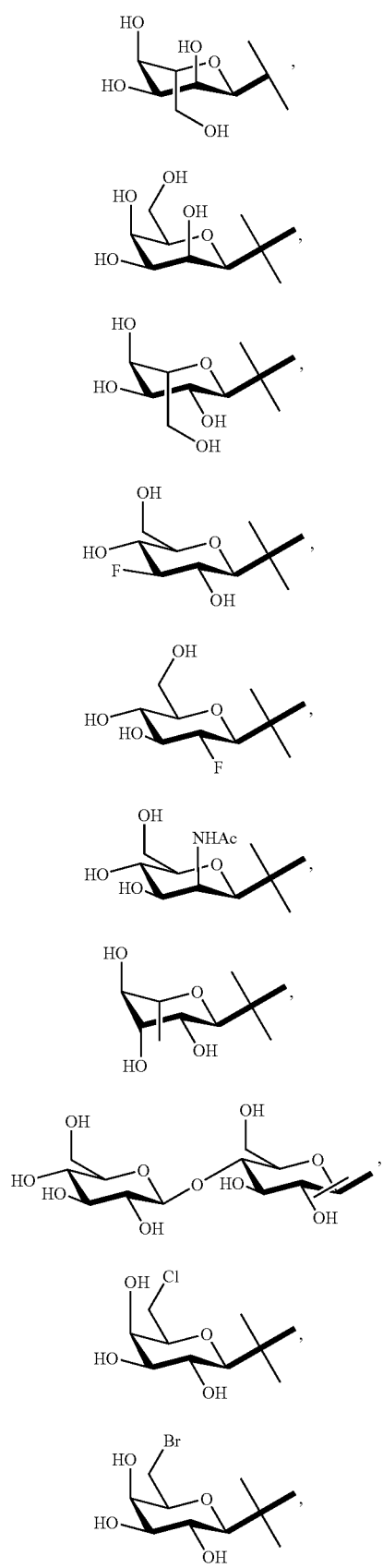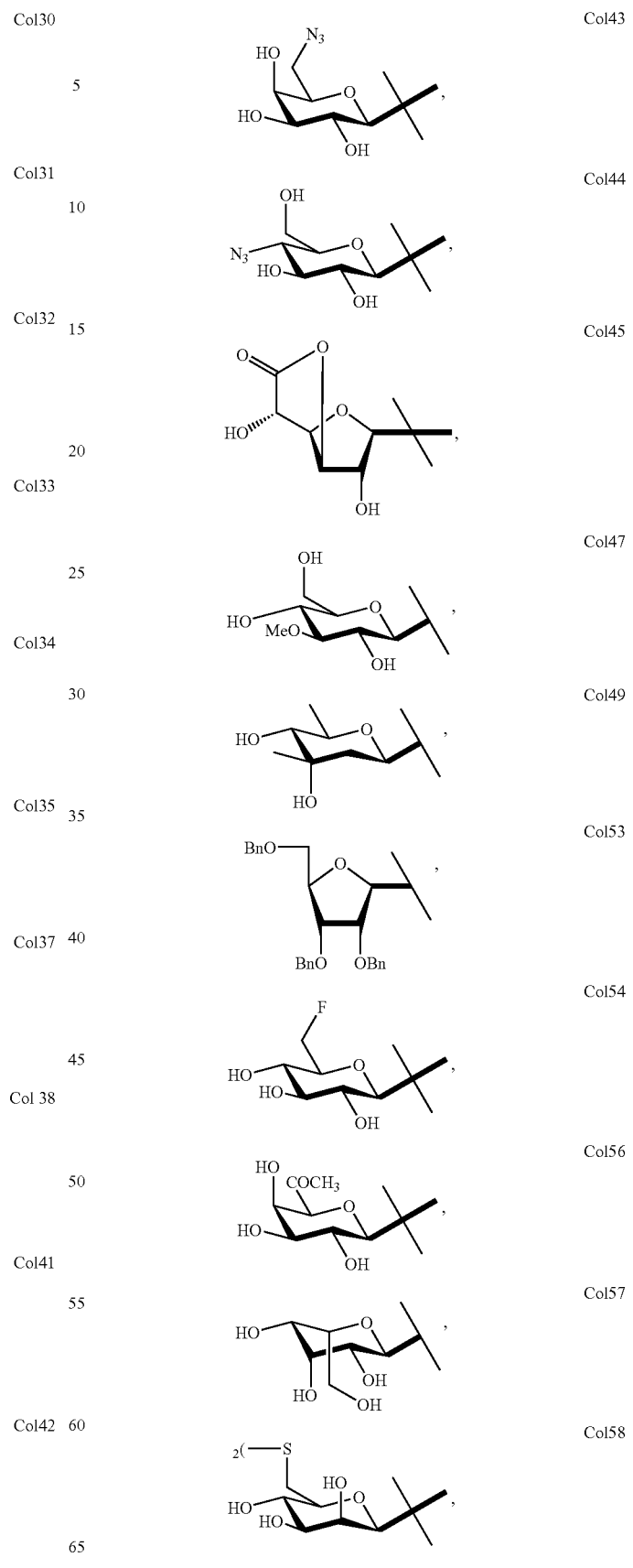

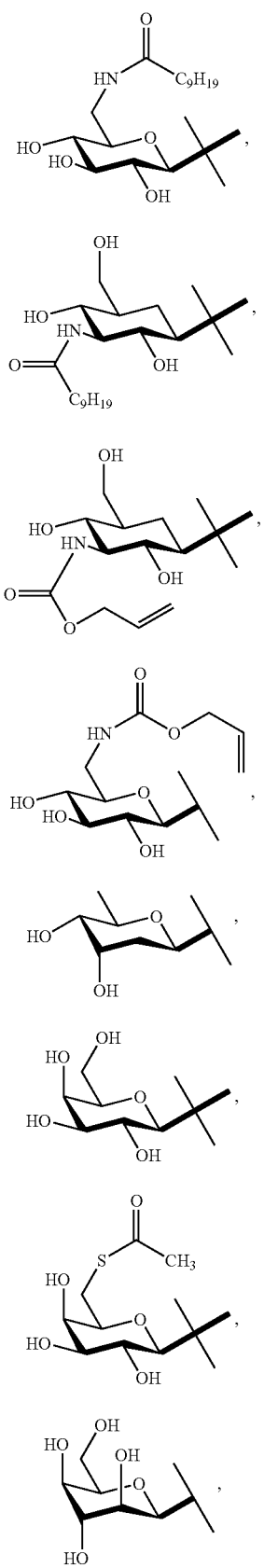
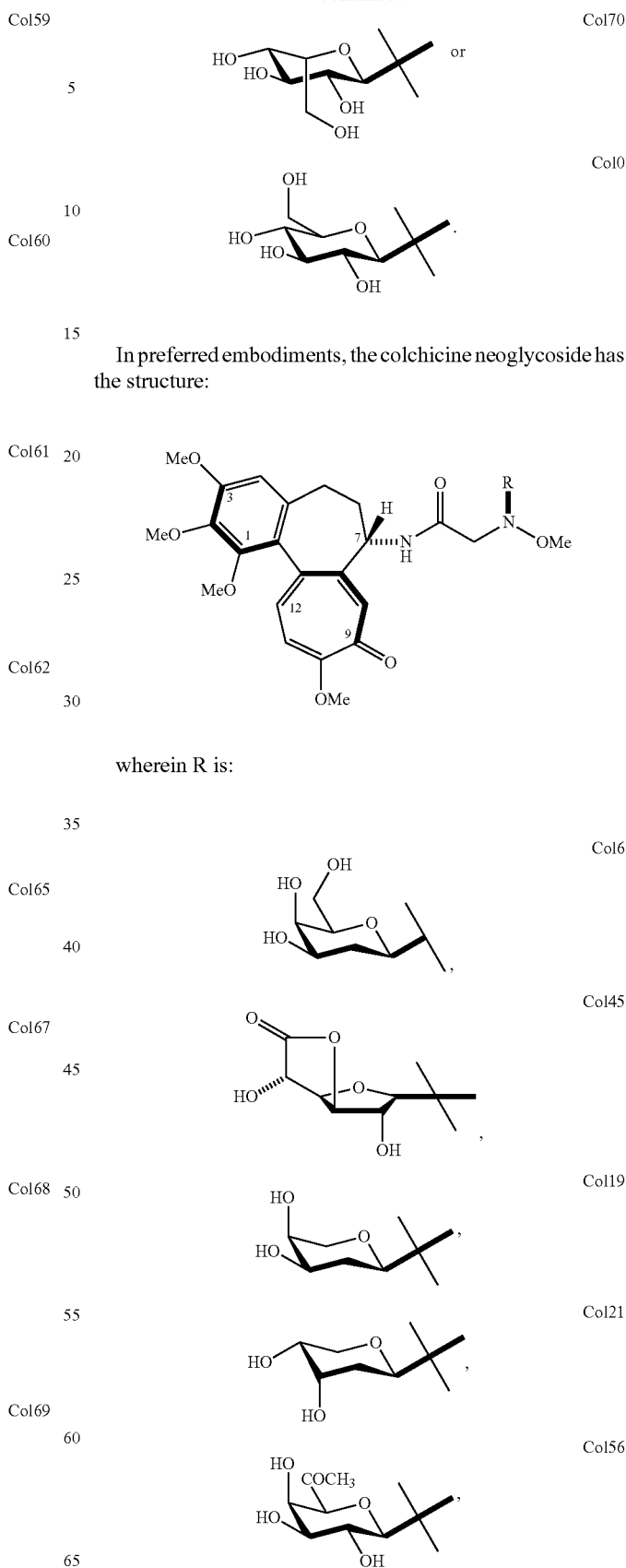
In preferred embodiments, the colchicine neoglycoside has the structure:
wherein R is:

-continued

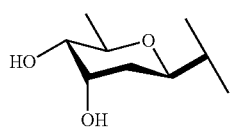

In another embodiment, the invention comprises an intermediate in the synthesis of colchicine neoglycosides, namely, a methoxyamine-appended colchicine according to the structure:

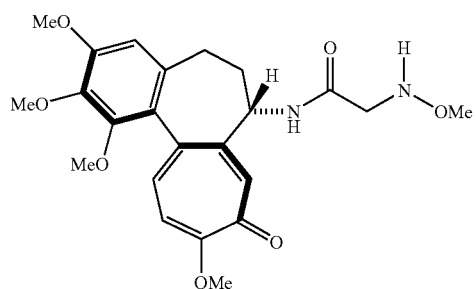

In yet another embodiment, the invention includes a method of synthesizing a colchicine neoglycoside according to the reaction:

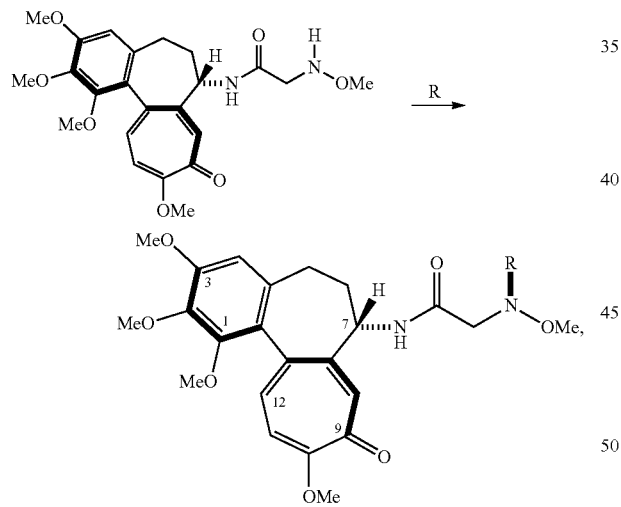

wherein R is:

Col1

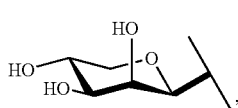

Col2

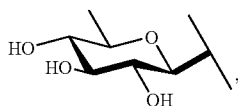

Col3

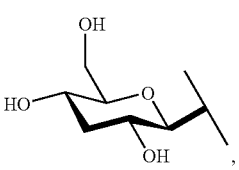

Col4

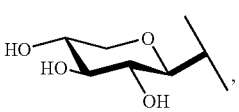

Col5

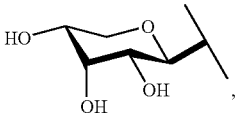

Col6

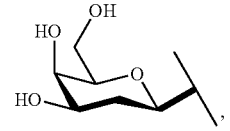

Col7

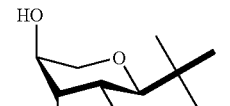

Col8

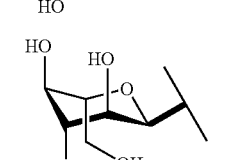

Col9

Col10

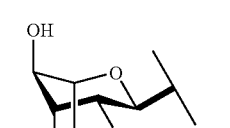

Col11

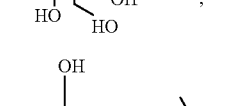

Col12

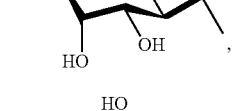

Col13

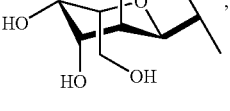

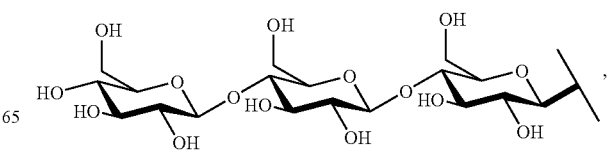

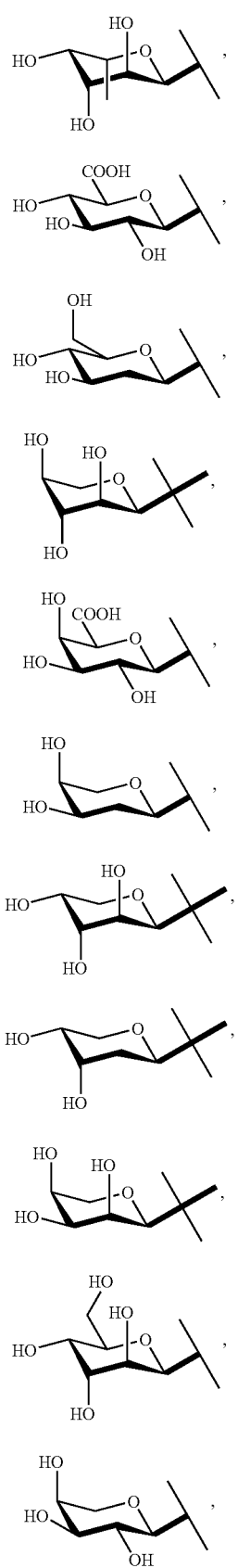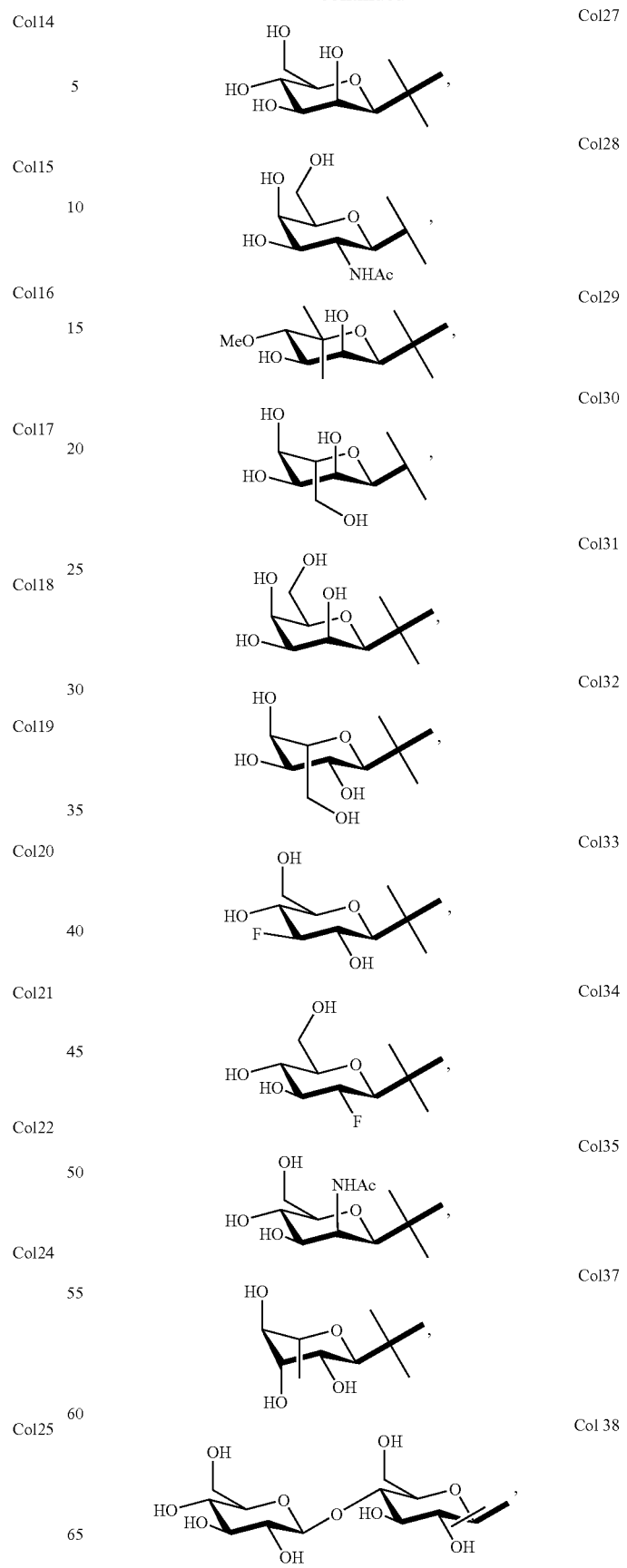

27
-continued

Col41, Col42, Col43, Col44, Col45, Col47, Col49, Col53, Col54, Col56

28
-continued

Col57, Col58, Col59, Col60, Col61, Col62, Col65, Col67, Col68

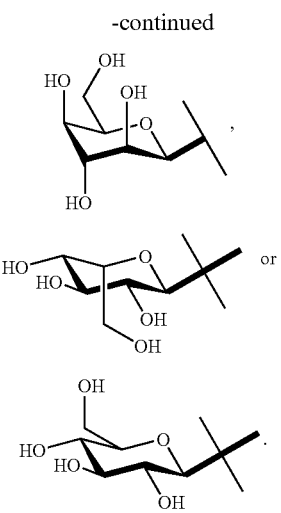

In some exemplary embodiments the reaction is carried out at 40° C. in the presence of 3:1 DMF/AcOH.

In another exemplary embodiment, the invention includes a method of treating cancer, arthritis, Mediterranean fever, amyloidosis, scleroderma, irritable bowel syndrome or gout comprising administering to a patient in need thereof a therapeutic amount of a colchicine neoglycoside as described and claimed herein in combination with other therapeutically effective drugs.

In some preferred embodiments, the other therapeutically effective drugs are selected from an alkaloid, an anthracycline, a taxane and combinations thereof. In some preferred embodiments, the alkaloid is colchicine. In other preferred embodiments the anthracycline is doxorubicin. In yet other preferred embodiments the taxane is paclitaxel.

This invention is not limited to the particular methodology, protocols, and reagents described, as these may vary. The terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

As used herein and in the appended claims, the singular forms "a," "an," and "the" include plural reference unless the context clearly dictates otherwise. As well, the terms "a" (or "an"), "one or more," "at least one," "comprising," "including," "characterized by" and "having" can be used interchangeably herein.

Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. As used herein, "administering" or "administration" includes any means for introducing a colchicines neoglycoside into the body, preferably into the systemic circulation. Examples include but are not limited to oral, buccal, sublingual, pulmonary, transdermal, transmucosal, as well as subcutaneous, intraperitoneal, intravenous, and intramuscular injection.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The colchicine neoglycoside, optionally comprising other pharmaceutically active compounds, can be administered to a patient either orally, rectally, parenterally, (for example, intravenously, intramuscularly, or subcutaneously) intracistemally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The colchicine neoglycoside according to the present invention may also contain adjuvants such as preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the colchicine neoglycosides can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions for rectal or vaginal administration can be prepared by mixing a colchicine neoglycoside and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the colchicine neoglycoside. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a colchicine neoglycoside according to the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the colchicine neoglycosides may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The colchicine neoglycosides of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the colchicine neoglycoside is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to treat the malady under treatment, directly or indirectly. The minimum amount varies with the identity of the colchicine neoglycoside.

In preferred embodiments, a pharmaceutical composition comprising a colchicine neoglycoside can be administered to a patient at dosage levels in the range of about 0.1 to about 7,000 mg per day. A preferred dosage range is about 1 to about 100 mg per day. In other embodiments, a pharmaceutical composition comprising a colchicine neoglycoside can be administered to deliver a dose of between one nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

Various exemplary embodiments of compositions and methods according to this invention are now described in the following examples. In these embodiments, specific products identified by Arabic numerals (e.g., 1, 2, 3, etc.) refer to the specific structures so identified in the following description. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

In an effort to identify novel methods for the glycorandomization of naturally occurring glycosylated compounds, the inventors set out to assess i) the potential impact of glycosylation upon natural products that naturally do not contain a carbohydrate moiety and ii) the utility of extending neoglycosylation to amine-bearing scaffolds. Colchicine (FIG. 1, (1)), the nonglycosylated model for the invention disclosed herein, inhibits tubulin polymerization causing metaphasic mitotic arrest which leads to rapid cell death. Toxicity limits its clinical use to the treatment of severe inflammatory episodes of gout, familial Mediterranean fever, and Behcet's disease. Only two colchicine 3-demethyl-3-glycosides have been reported (Bombardelli, E.; Fontana, G. PCT Int. Appl. 2004, WO 2004111068 A1) and thus, the effects of glycosylation upon this natural product remain largely unknown. Herein the inventors disclose the synthesis of a fifty seven-member differentially-glycosylated colchicine library. Cytotoxicity screens revealed neoglycosylation to modulate the specificity and potency of (1) and compounds were identified which, unlike 1 (a destabilizer), stabilized tubulin polymerization.

The reaction of seventy unprotected, diversely-functionalized, free reducing sugars with methoxyamine-appended colchicine led to the production of a fifty seven-member glycorandomized library. High-throughput cytotoxicity assays revealed glycosylation to modulate specificity and potency. Neoglycosylated library members were also identified which, unlike colchicine, the parent natural product (a destabilizer), stabilized in vitro tubulin polymerization in a manner similar to taxol. This invention provides a hitherto unappreciated extension of neoglycosylation toward amine-bearing scaffolds and the potential benefit of glycosylating non-glycosylated natural products as illustrated in FIG. 1.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described.

EXAMPLES

Example 1

Synthesis of a Colchicine Neoglycoside Library

Figure 2:
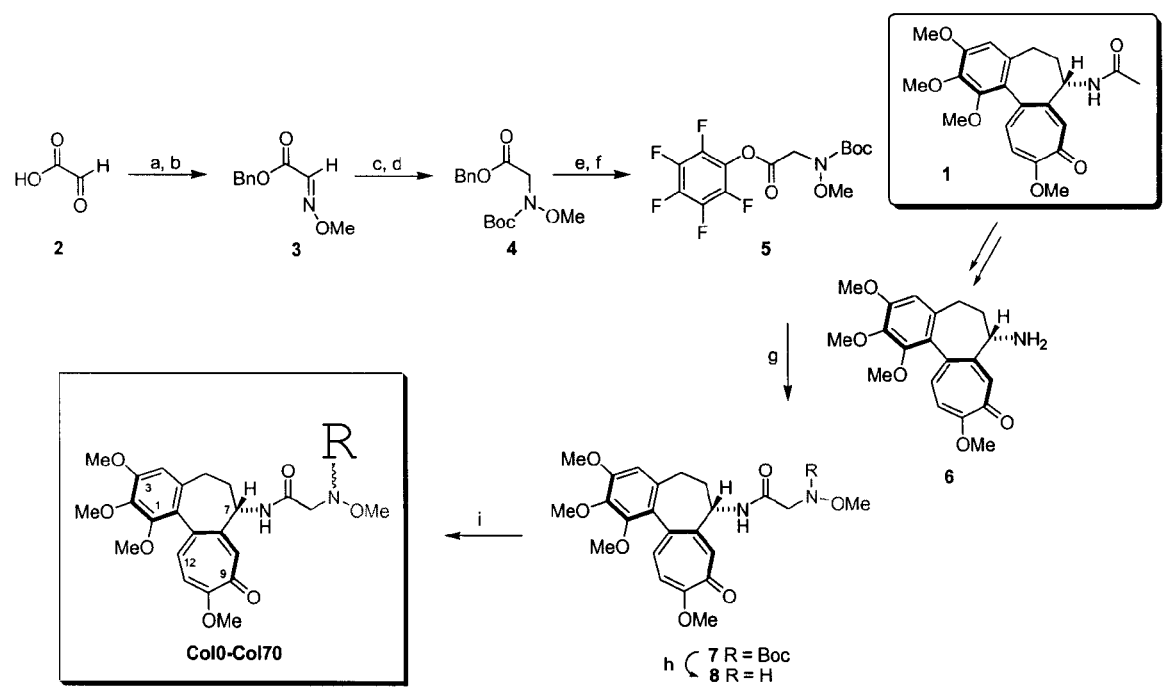
FIG. 2 shows the synthesis of the methoxyamine-tethered aglycon 8. Reagents and conditions: (a) MeONH$_2$—HCl, Py, MeOH, rt, 1 h, 99%; (b) BnBr, NaHCO$_3$, DMF, 70° C., 16 h, 80%; (c) BH$_3$-Py, 6 M HCl in EtOH, 15 h, 88%; (d) (Boc)$_2$O, NaHCO$_3$, THF/H$_2$O (2:1), 16 h, 96%; (e) H$_2$, Pd/BaSO$_4$, EtOH, 1.5 h, 99%; (f) pentafluorophenol, diisopropyl carbodiimide, CH$_2$Cl$_2$/dioxane (1:1) rt, 16 h, 80%; (g) CH$_2$Cl$_2$, 20 h, rt, 96% (h) TFA, MeOH, 3 days, 78%; (i) diverse sugars, DMF/AcOH, 24 h, 40° C., >65%.
Figure 3:
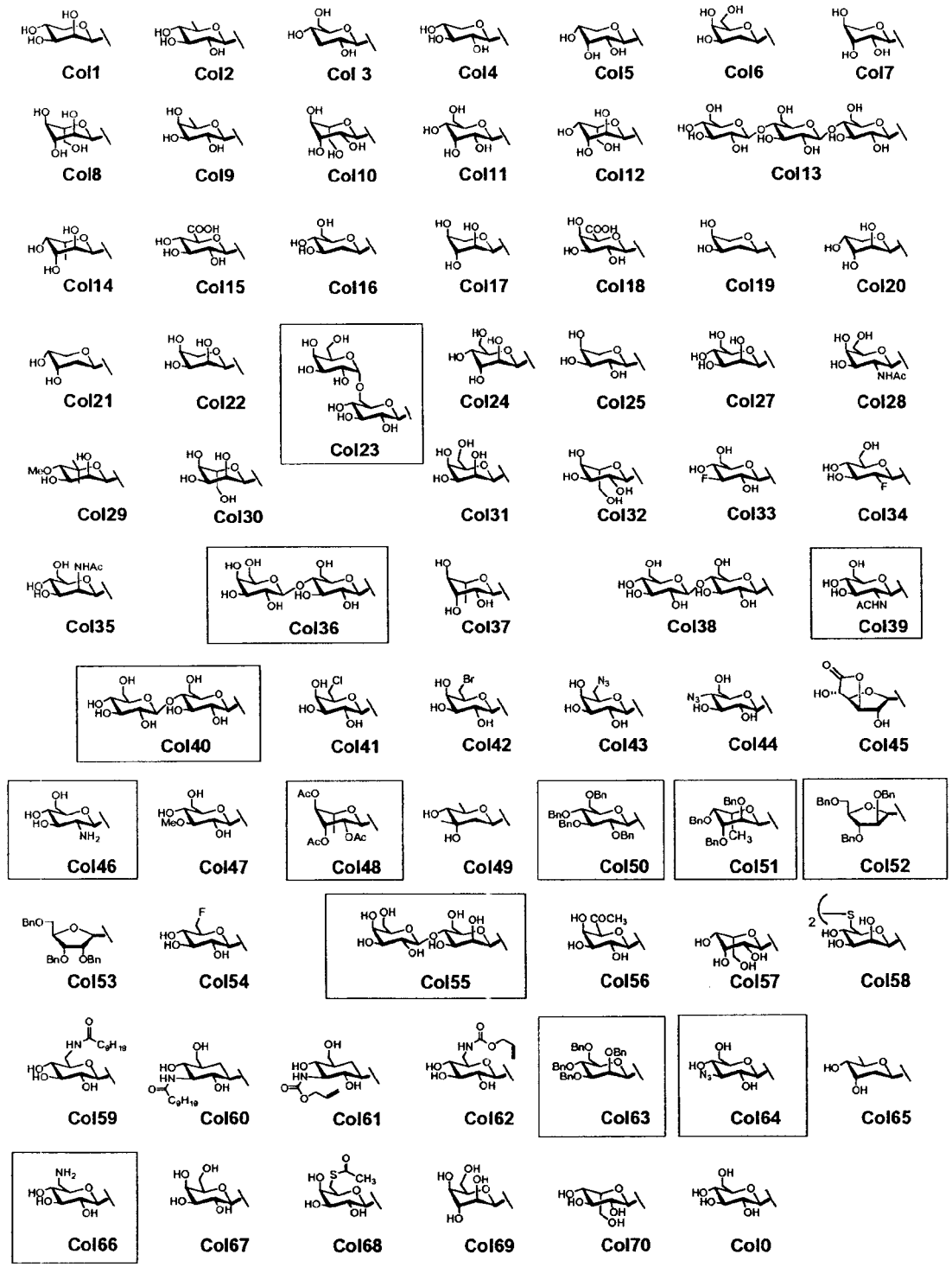
FIG. 3 shows a colchicine-neoglycoside library according to the present invention (the boxed neoglycosides represent failed reactions)
Figure 4:
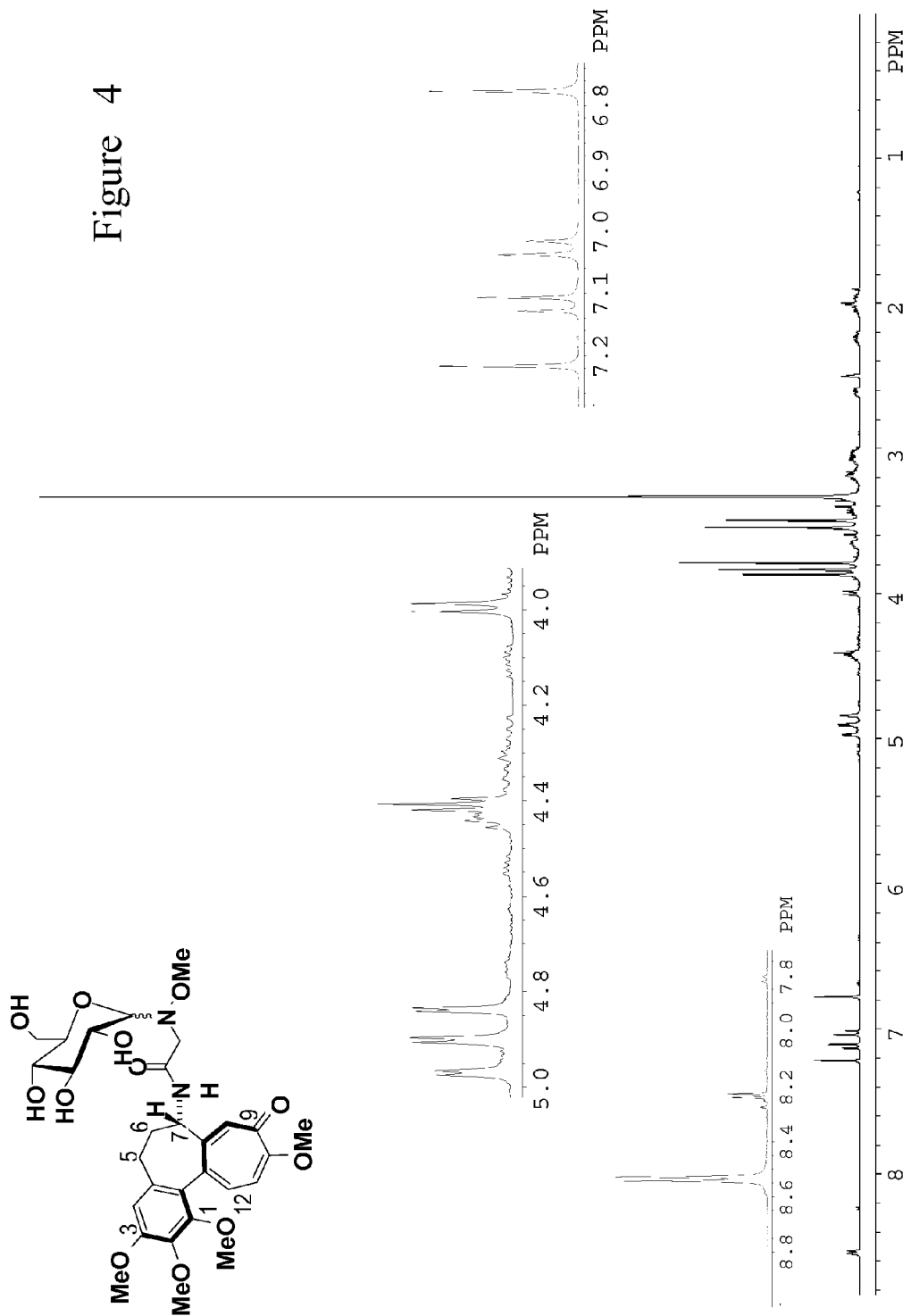
FIG. 4 is an $^1$H NMR spectrum of Col0 (500 MHz, DMSO-d$_6$)
Figure 5:
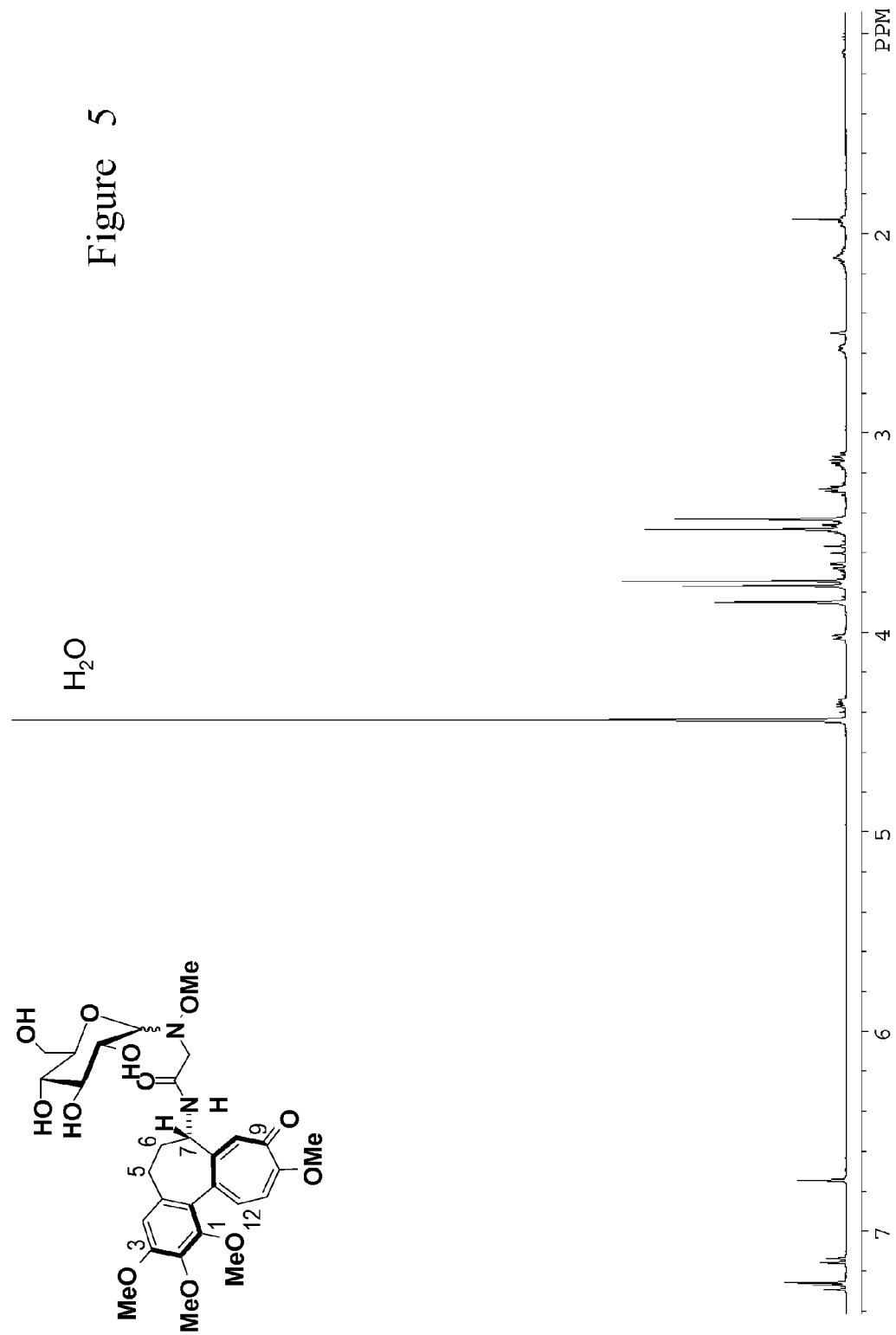
FIG. 5 is an $^1$H NMR spectrum of Col0 (500 MHz, 1:1 DMSO-d$_6$: D$_2$O)
Figure 6:
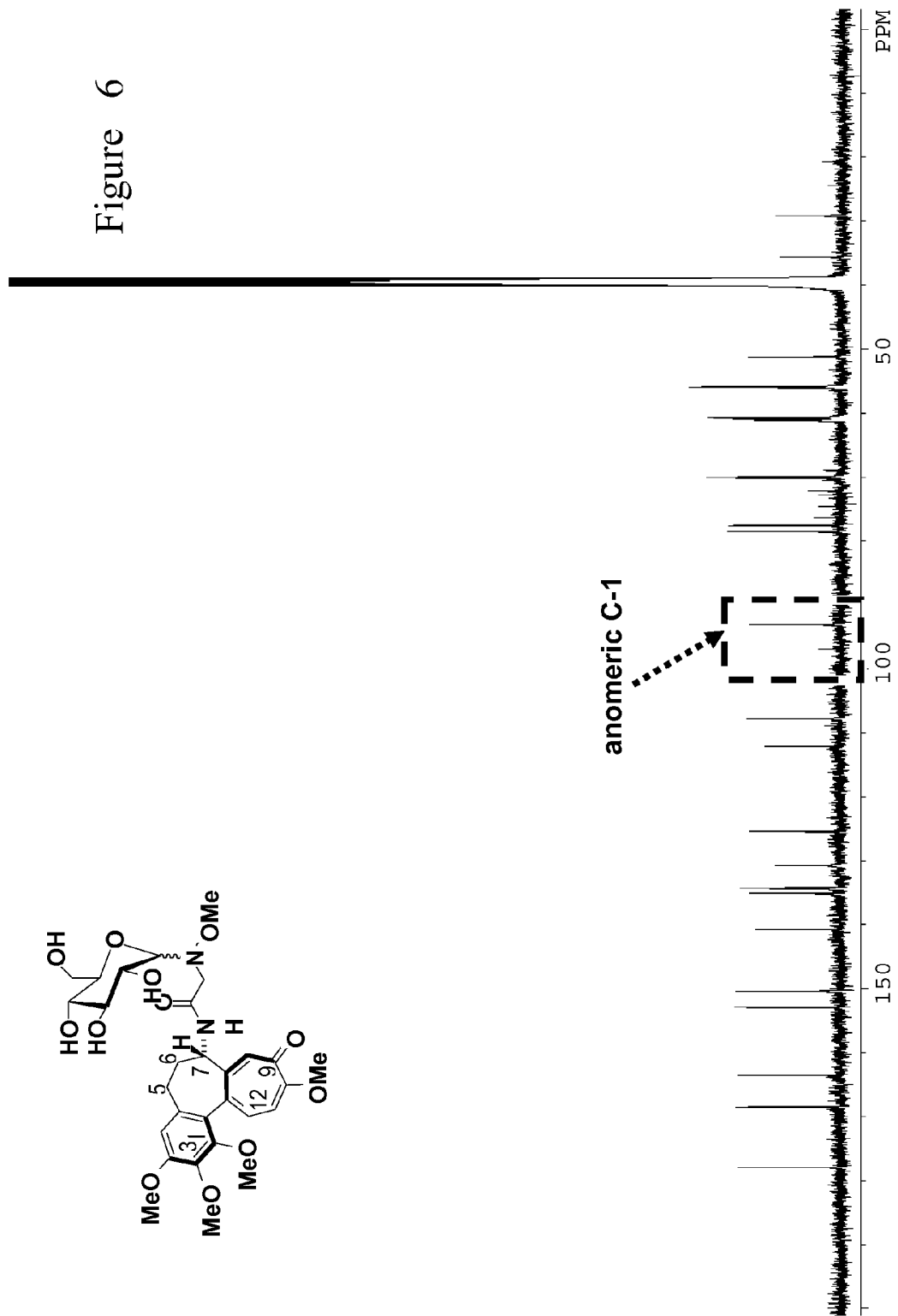
FIG. 6 is a $^{13}$C NMR spectrum of Col0 (100 MHz, DMSO-d$_6$)
Figure 7:
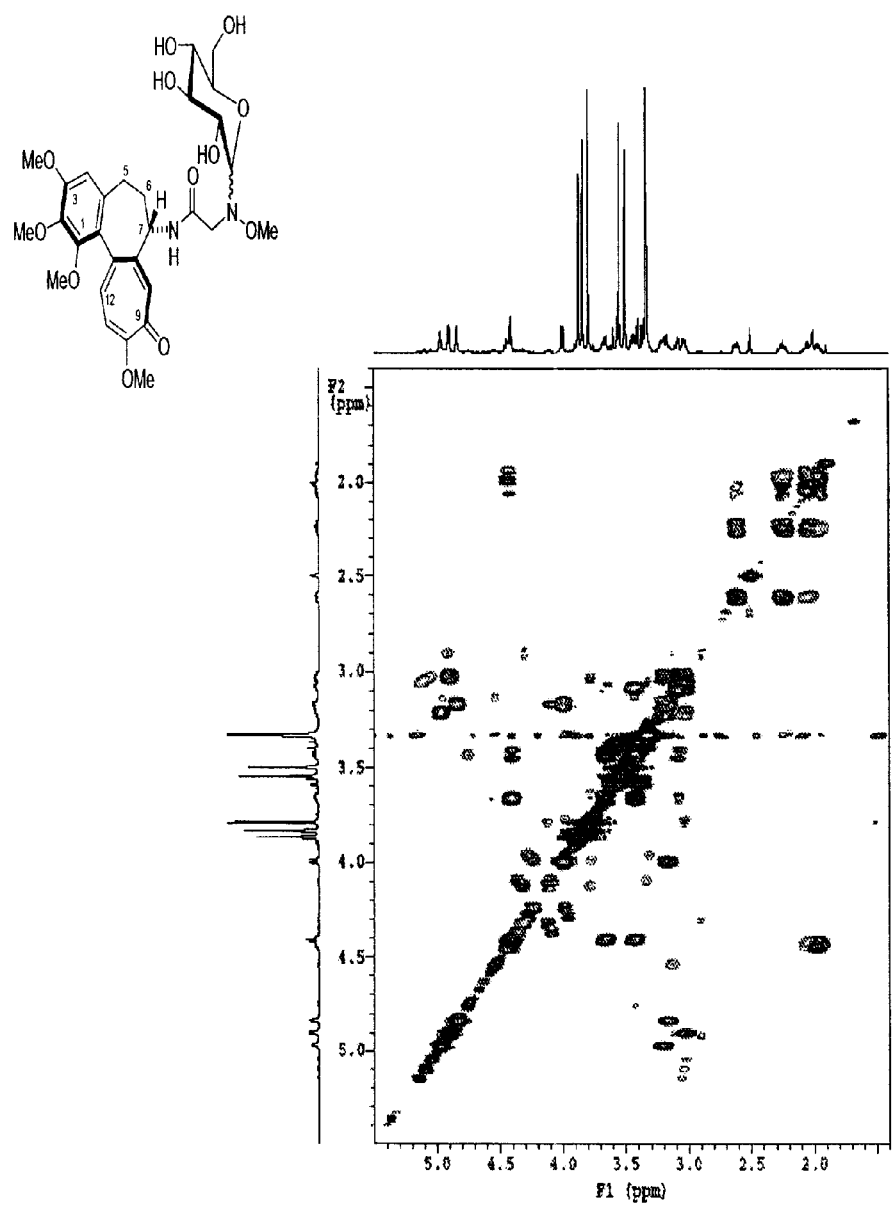
FIG. 7 is a $^{13}$C NMR spectrum of Col0 (100 MHz, DMSO-d$_6$)
Figure 8:
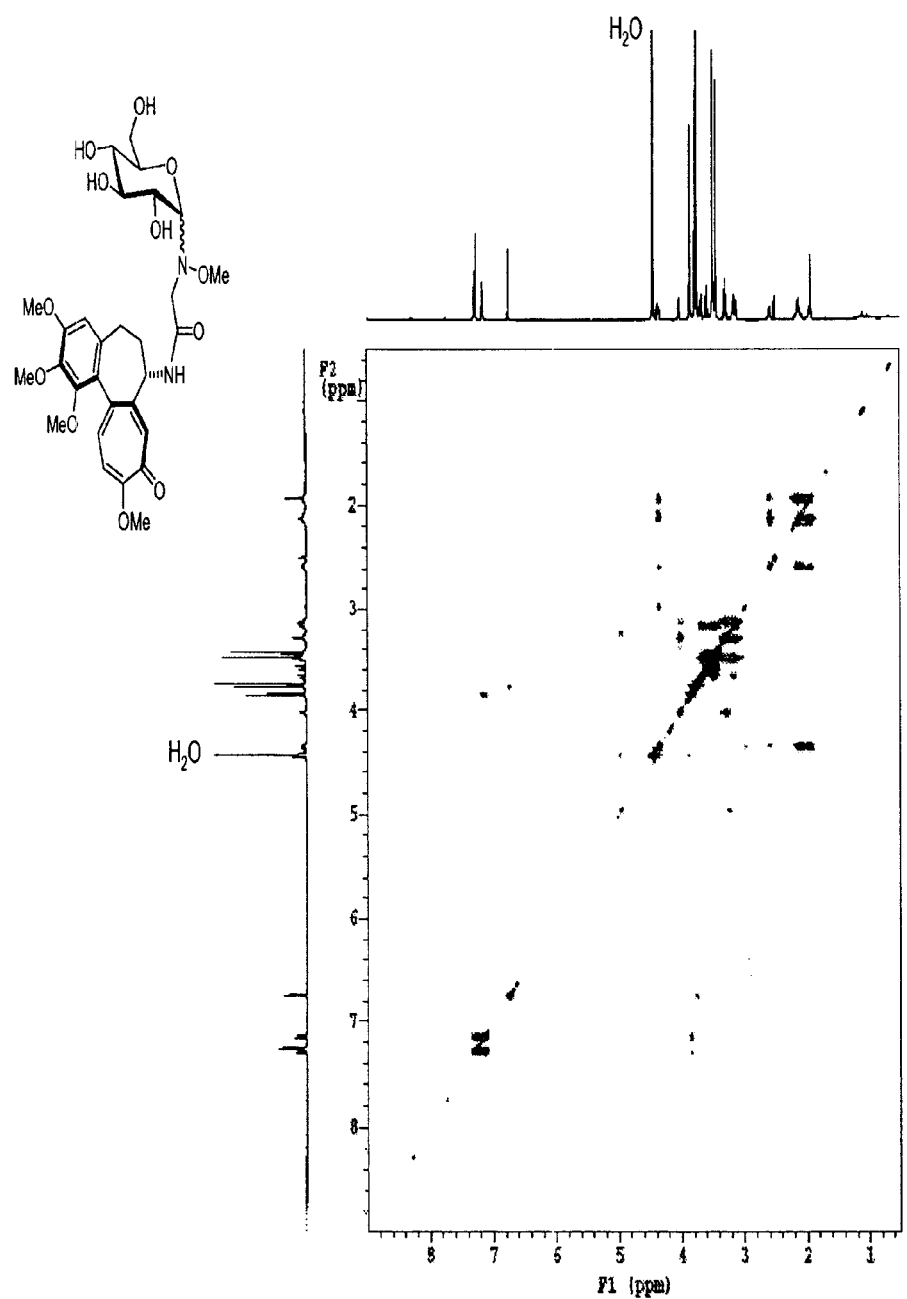
FIG. 8 is a gCOSY spectrum of Col0 (500 MHz, 1:1 DMSO-d$_6$: D$_2$O)
Figure 9:
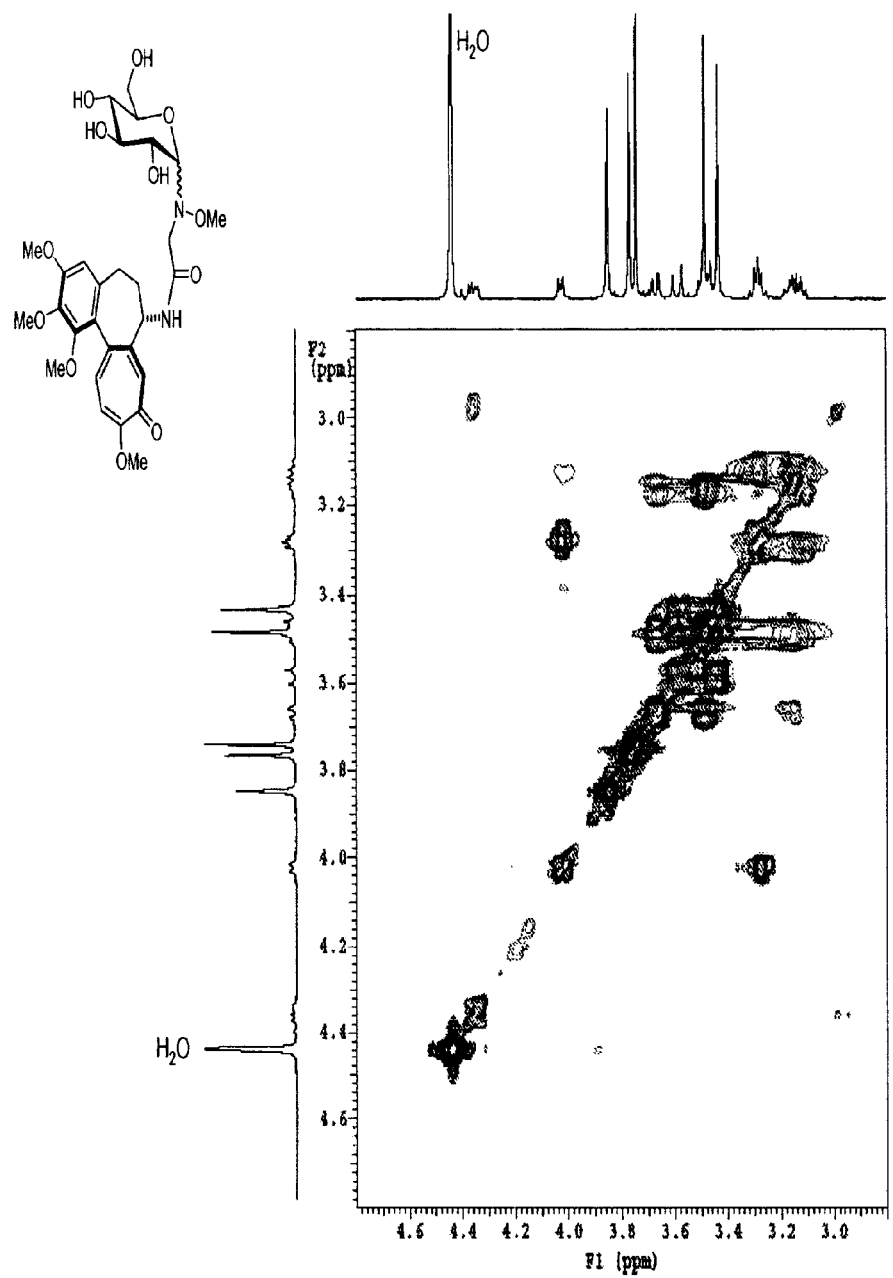
FIG. 9 is a gCOSY spectrum of Col0 (500 MHz, 1:1 DMSO-d$_6$: D$_2$O)
Figure 10:
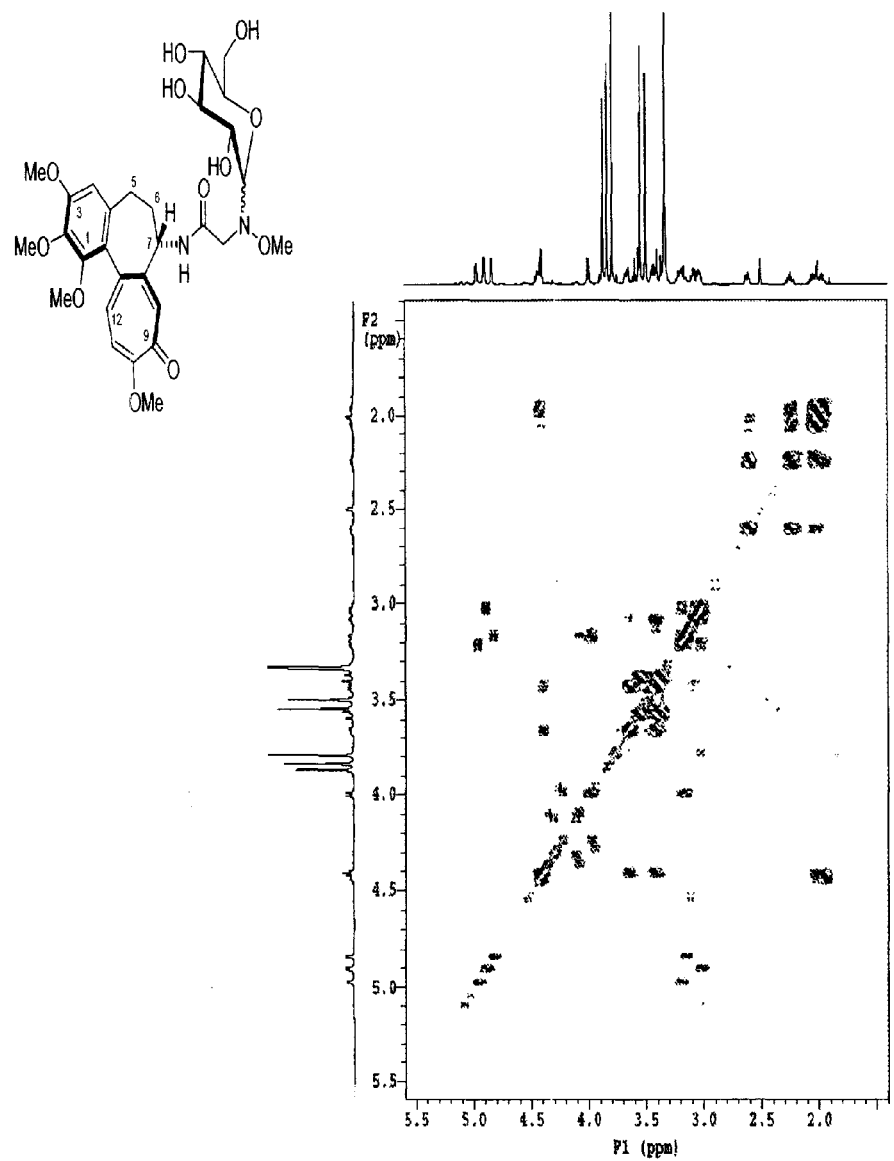
FIG. 10 is a gDQCOSY spectrum of Col0 (500 MHz, DMSO-d$_6$)
Figure 11:
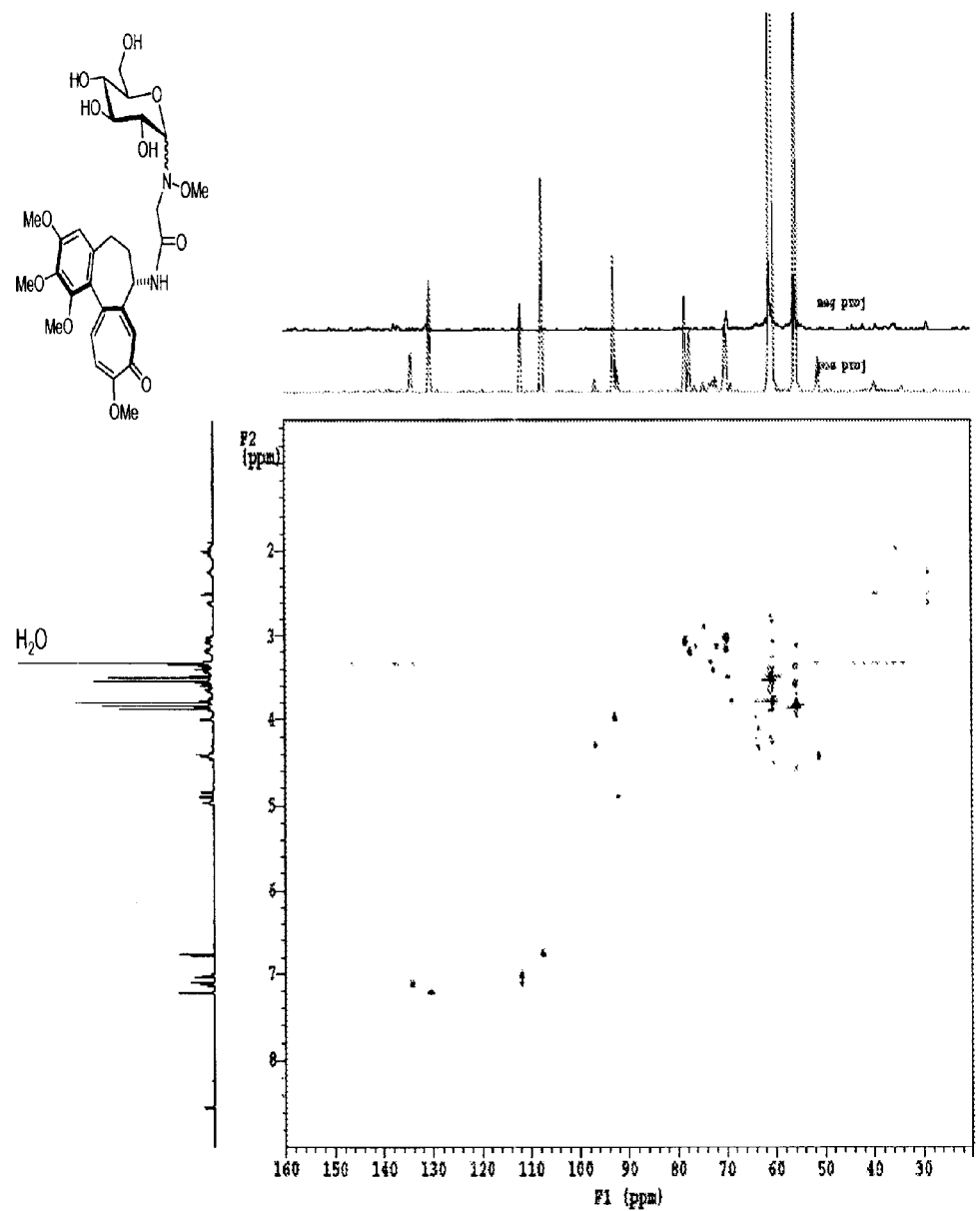
FIG. 11 is a gHSQC spectrum of Col0 (500 MHz, DMSO-d$_6$)
Figure 12:
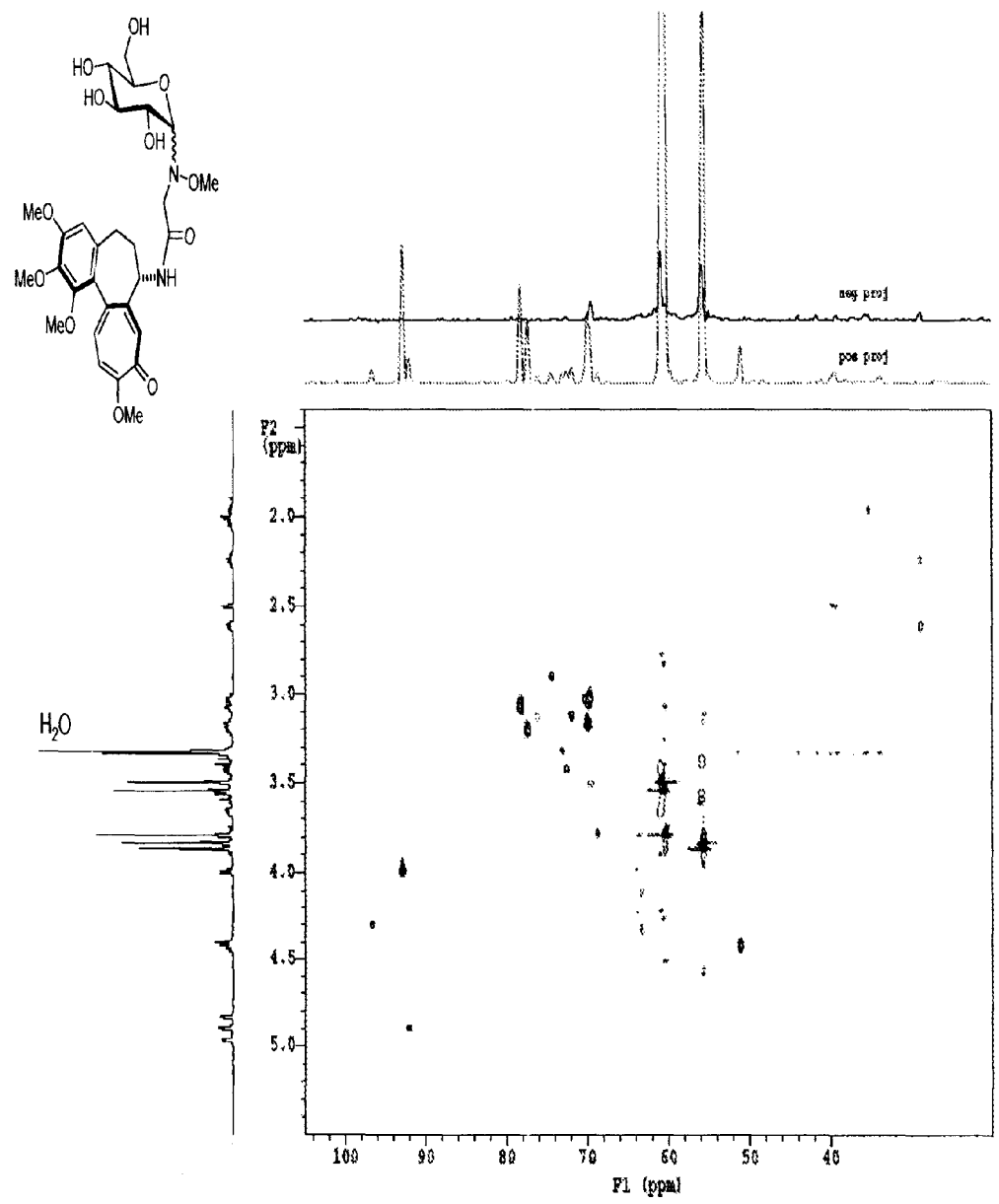
FIG. 12 is a gHSQC spectrum of Col0 (500 MHz, DMSO-d$_6$).

The synthesis of the methoxyamine-tethered aglycon (8) is illustrated in FIG. 2 (8 steps, 40% overall yield). Reaction of glyoxalic acid (2) with methoxyamine followed by benzylation resulted in the formation of methoxyimino acetic acid benzyl ester (3). Reduction of (3) with borane-pyridine complex followed by Boc protection afforded the intermediate (4). Reductive debenzylation of (4) and esterification with pentafluorophenol furnished the activated ester-linker (5). Finally treatment of (6) with (5) in $CH_2Cl_2$ followed by deprotection gave the desired methoxyamine-appended aglycon (8). The chemoselective neoglycosylation reaction of (8) with D-glucose in DMF/AcOH smoothly provided the corresponding colchicine neoglucoside in 65% yield. Consistent with previous reports (Langenhan, J. M. et al., Proc. Natl. Acad. Sci. U.S.A. 2005, 102, 12305) the reaction with D-glucose favored the β-isomer (87:13 β:α). Using conditions based upon this successful pilot reaction, the reaction of seventy unprotected, diverse, free reducing sugars with (8) gave a library of fifty-eight colchicine neoglycosides with yields ranging from 14-78% (average overall 51%). All library members were purified and LC-MS was employed to assess purity (96.2%, average) and confirm identity.

The cytotoxicity of the library members was assessed in nine human cancer cell lines representing a broad range of carcinomas including breast, colon, CNS, liver, lung, and ovary, and a mouse mammary normal epithelial control cell line. Three standards—(1) (the parent tubulin destabilizer), paclitaxel (a representative tubulin stabilizer) and doxorubicin (a representative tubulin non-interacting cytotoxin)—were also examined. All library members displayed $IC_{50}$s below the 'non-toxic' threshold of 10 μM (defined as three orders of magnitude greater than the $IC_{50}$ of the parent molecule colchicine) in at least one cell line. Fifteen library members (including Col6, Col19, Col21, Col45, Col56 and Col65, Table 1) displayed $IC_{50}$s of less than 1 μM in at least one cell line with some within this subset displaying unique cell line specificities.

For example, Col6 displayed an $IC_{50}$ of 381 nM in SK-OV-3 cells with potencies in all other cell lines ranging from 691 nM-1.12 μM. In a similar fashion, Col45 displayed 403 nM-529 nM potencies in three cell lines (ADR-Res, SF-268 and HCT-116) with decreased potencies (exceeding ~900 nM) in all other cell lines examined. In contrast, the parent 1 displayed a nearly equivalent indiscriminate level of potency in five of the ten cell lines tested, including SK-OV-3 (ranging from 22 nM-35 nM) as did neoglycosides Col19 and Col21, albeit both roughly one order of magnitude less potent than (1). It should be noted that while the best neoglycosides (Col19 and Col21) displayed roughly a 10-fold reduction in potency, the $IC_{50}$s of these colchicine neoglycosides still fall within a range of the clinically-relevant cytotoxins doxorubicin and paclitaxel. Doxorubicin and paclitaxel represent members of the anthracycline and taxane families of drugs, respectively, currently used to treat cancer and restenosis. Though each drug has been found efficacious on its own to be used in therapy, currently each is being evaluated for its use in combination with other drugs such as, for example, carboplatin vinorelbine, to identify even more effective uses.

TABLE 1

| | | | | | | |
|---|---|---|---|---|---|---|
| Activities of colchicine neoglyosides. | | | | | | |
| compound name | compound structure[a] | $IC_{50}$ (Du145)[b] | $IC_{50}$ (HCT-116)[b] | $IC_{50}$ (Hep3B)[b] | $IC_{50}$ (SF-268)[b] | $IC_{50}$ (SK-OV-3)[b] |
| colchicine | 1 | 0.022 | 0.091 | 0.329 | 0.035 | 0.024 |
| Col6 | | 0.958 | 0.792 | 1.124 | 0.691 | 0.381 |
| Col45 | | 0.939 | 0.529 | 0.962 | 0.462 | 0.887 |
| paclitaxel | | 0.290 | 0.275 | 0.166 | 0.315 | 0.034 |
| Col19* | | 0.262 | 0.431 | 0.437 | 0.575 | 0.538 |

TABLE 1-continued

| compound | structure | | | | | |
|---|---|---|---|---|---|---|
| Col21* | (structure) | 0.294 | 0.344 | 1.291 | 0.349 | 0.296 |
| doxorubicin | | 0.339 | 0.524 | 0.268 | 0.385 | 0.621 |
| Col56 | (structure) | 1.094 | 0.669 | 2.228 | >1 | 1.182 |
| Col65 | (structure) | 0.939 | 0.897 | 1.875 | 0.665 | 1.031 |

| compound name | $IC_{50}$ (ADR-RES)[b] | $IC_{50}$ (NCI-H460)[b] | $IC_{50}$ (A549)[b] | tubulin polymeriz.[c] | synergy (colchicine)[d] | synergy (paclitaxel)[d] |
|---|---|---|---|---|---|---|
| colchicine | 0.027 | 0.022 | 0.118 | D | | ++ |
| Col6 | 0.887 | 0.948 | 0.942 | D | -- | + |
| Col45 | 0.403 | 1.024 | 1.055 | D | --- | ++++ |
| paclitaxel | 0.043 | 0.105 | 0.075 | S | +++ | |
| Col19* | 0.315 | 0.191 | 0.636 | S | +++ | ---- |
| Col21* | 0.209 | 0.355 | 0.248 | S | + | --- |
| doxorubicin | 0.174 | 1.001 | 0.770 | no effect | nd | nd |
| Col56 | 0.994 | 1.094 | 2.094 | no effect | nd | nd |
| Col65 | 0.694 | 0.744 | 2.301 | no effect | nd | nd |

[a] the saccharide portion of the library member is represented; [b] cytoxicity (μM$^{-1}$) as determined by cell titer-glo and calcein AM assays (see Supplemental Online Material for assay parameters); [c] the results of tubulin polymerization assays where 'D' designates destabilizer and 'S' designates stabilizer (see Supplemental Online Material for assay parameters);
[d] synergism or antagonism in drug combination studies with the parent 1 (a representative destabilizer) or paclitaxel (a representative stabilizer) analyzed via the Chou-Talalay Method (see reference 11) the results of synergy assays - legend (combination index): ++++ (strong synergism, CI 0.1-0.3), +++ (synergism, CI 0.3-0.7), ++ (moderate synergism, CI 0.7-0.85, + (slight synergism, CI 0.85-0.9), - (slight antagonism, CI 1.1-1.2), -- (moderate antagonism, CI 1.2-1.45), --- (antagonism, CI 1.45-3.3), ---- (strong antagonism, CI 3.3-10); *library member contains both pyranose and furanose forms (see reference 12).

To assess how these structural modifications affect the ability of library members to modulate tubulin polymerization, a fundamental activity of (1), the same fifteen 'hits' were submitted to a secondary in vitro tubulin polymerization assay (Bonne, D. et al., Biol. Chem. 1985, 260, 2819). As expected, eight compounds (including Col6 and Col45, Table 1) exhibited effects on microtubules consistent with the destabilizing effects of (1). However, three compounds (including Col56 and Col65, Table 1) had no apparent effect on tubulin polymerization (similar to the standard doxorubicin), and surprisingly, two compounds (Col19 and Col21, Table 1) exhibited effects on microtubules consistent with the stabilizing effects of paclitaxel.

Drug combination assays were subsequently performed to determine if the mechanism of action of tubulin binding by (1) had been affected for compounds Col19 and Col21. Consistent with the in vitro tubulin polymerization results, Col19 and Col21 showed synergism with the parent (1) and antagonism with paclitaxel, suggesting the Col19/21-tubulin interaction mirrors that of paclitaxel-tubulin. Many synthetic and natural product small molecules are known to stabilize or destabilize tubulin polymerization (Jordan, M. A.; Wilson, L. Nat. Rev. Cancer 2004, 4, 253). However, the results disclosed herein are the first examples of interconverting these two distinct mechanisms via simple synthetic derivatization. Cumulatively, these examples highlight an extension of neoglycosylation toward amine-bearing scaffolds and illustrate a desirable benefit to glycosylating non-glycosylated natural products.

Example 2

General Methods

Proton nuclear magnetic resonance ($^1$H and $^{13}$C NMR) spectra were recorded in deuterated solvents on Varian Unity-Inova 400 MHz or 500 MHz spectrometers. Chemical shifts are reported in parts per million (ppm, δ) relative to tetramethylsilane (0.00) for d-chloroform, or the residual protic solvent peak for other solvents. $^1$H NMR splitting patterns with observed first order coupling are designated as singlet (s), doublet (d), triplet (t), or quartet (q). Splitting patterns that could not be interpreted or easily visualized are designated as multiplet (m), broad (br), or apparent (a). Mass spectra (MS) were obtained with the Agilent 1100 HPLC-MSD SL Ion Trap Mass Spectrometer using electrospray ionization. High resolution mass spectrometry data for new compounds (Table 2) were obtained at the University of Wisconsin Biotechnology Center Mass Spectrometry Facility and are provided in Table 3 (See EXAMPLE 9). Commercially available reagents and solvents were used without further purification. Analytical thin layer chromatography (TLC) was carried out on TLC plates pre-coated with silica gel 60 (250 μm layer thickness). Visualization was accomplished using either a UV lamp or potassium permanganate stain (2 g $KMnO_4$, 13.3 g $K_2CO_3$, 2 mL 2M NaOH, 200 mL $H_2O$). Flash column chromatography was performed on 40-60 μm silica gel (230-400 mesh). Solvent mixtures used for TLC and flash column chromatography are reported in v/v ratios

Example 3

Preparing benzyl(2-methoxyimino)acetate (3)

Benzyl (2-methoxyimino)acetate (3) was prepared as follows: methoxylamine hydrochloride salt (75.0 g, 0.90 mol) was added to a stirred solution of glyoxylic acid monohydrate (75.1 g, 0.82 mol) in pyridine/MeOH (1:1, 1.4 L) under argon. The reaction mixture was stirred at room temperature for one hour and quenched with saturated aqueous $NH_4Cl$. The aqueous layer was extracted with EtOAc (3×, 700 mL), the organic layers were combined and dried over $Na_2SO_4$ and concentrated. Purification of the crude material by flash chromatography (8:1 EtOAc/MeOH) furnished methoxyimino-acetic acid as a colorless solid in 83.3 g, 99% yield. $R_f$=0.57 (50% $CHCl_3$/MeOH); $^1H$ δ ($CD_3OD$): 7.45 (s, 1H), 3.98 (s, 3H); $^{13}C$ δ ($CD_3OD$): 163.8, 141.1, 62.5; Electrospray ionization-MS m/z $[M-H]^-$ calculated for $C_3H_4NO_3$, 102.0; observed 102.0.

To methoxyimino-acetic acid (21.0 g, 202.3 mmol) in DMF (65 ml) was added $NaHCO_3$ (68.0 g, 0.81 mol) and BnBr (96.1 ml, 0.18 mol). The reaction mixture was allowed to stir at room temperature for one hour and at 70° C. for sixteen h. After the reaction was complete, based on TLC, the mixture was cooled to 0° C. and quenched with diH2O. The aqueous layer was extracted with EtOAc (3×, 500 ml) and the combined organic layers were washed with brine (2×, 500 ml) dried over $Na_2SO_4$ and filtered. The solvent was removed under reduced pressure and the crude product was purified by flash chromatography (5% EtOAc/Hexanes) to furnish benzyl (2-methoxyimino)acetate (3) (31.2 g, 80%) as colorless oil. Rf=0.61 (20% EtOAc/Hexanes); $^1H$ δ ($CDCl_3$): 7.52 (s, 1H), 7.41 (m, 5H), 5.29 (s, 2H), 4.05 (s, 3H); $^{13}C$ δ 161.5, 140.3, 135.0, 128.4, 128.36, 128.34, 66.9, 63.3; Electrospray ionization-MS m/z $[M+Na]^-$ calculated for $C_{10}H_{11}NO_3Na$, 216.0; observed 216.1.

Example 4

Preparing benzyl[N-(tert-butoxycarbonyl)-N-methoxy-amino]acetate (4)

Benzyl [N-(tert-Butoxycarbonyl)-N-methoxy-amino]acetate (4) was prepared as follows: borane-pyridine complex (8.3 mL, 66.1 mmol, 8 M solution in pyridine) was added to a solution of benzyl (2-methoxyimino) acetate (8.5 g, 43.8 mmol) in EtOH (5 mL) at 0° C. under argon atmosphere. To this solution, 6 M HCl in ethanol (65 mL) was added in a dropwise fashion over a period of three h. The reaction mixture was stirred overnight at room temperature and neutralized (pH=7) via drop wise addition of saturated aqueous NaOH solution at 0° C. After removal of the solvent in vacuo, the crude residue was partitioned between water/$CH_2Cl_2$ (1:1, 400 mL). The aqueous layer was extracted with $CH_2Cl_2$ (3×, 150 mL), the combined organic layers were dried over $Na_2SO_4$, filtered, and concentrated to furnish the crude residue. Purification of the crude material by flash chromatography (20% EtOAc/petroleum ether) furnished 7.5 g (88%) of benzyl (2-methoxyamino) acetate as colorless oil. $R_f$=0.46 (20% EtOAc/petroleum ether); $^1H$ δ ($CDCl_3$): 7.36 (m, 5H), 5.19 (s, 2H), 4.64 (s, 1H), 3.64 (s, 2H), 3.53 (s, 3H); $^{13}C$ δ 171.2, 135.7, 128.9, 128.7, 128.6, 67.1, 61.8, 53.2; Electrospray ionization-MS m/z $[M+Na]^-$ calculated for $C_{10}H_{13}NO_3Na$, 218.0; observed 218.0.

$NaHCO_3$ (6.5 g, 76.9 mmol) was added to a solution of benzyl (2-methoxyamino) acetate (6.0 g, 30.7 mmol) in THF/$H_2O$ (2:1, 50 mL) and the mixture stirred for twenty minutes. $(Boc)_2O$ (13.4 g, 61.5 mmol) was added to this stirred solution, and the reaction was allowed to continue, with stirring, for sixteen hours. Upon completion (as determined via TLC), the reaction mixture was diluted with dd$H_2O$ (100 mL) and diethyl ether (100 mL). The aqueous layer was extracted with diethyl ether (3×, 150 mL), the combined organic layers were washed with 1 M aqueous HCl (2×, 100 mL), dried over $Na_2SO_4$, filtered and concentrated in vacuo. Purification of the crude material by flash chromatography furnished 8.73 g, 96% of the pure Benzyl [N-(tert-Butoxycarbonyl)-N-methoxy-amino]acetate (4). $R_f$=0.71 (20% EtOAc/petroleum ether); $^1H$ δ ($CDCl_3$): 7.33 (b, 5H), 5.16 (bs, 2H), 4.19 (s, 2H), 3.69 (s, 3H), 1.44 (s, 9H); $^{13}C$ δ 168.2, 156.3, 135.1, 128.3, 128.1, 128.1, 81.8, 66.7, 62.4, 51.3, 27.9; Electrospray ionization-MS m/z $[M+H]^+$ calculated for $C_{15}H_{22}NO_5$, 318.1; observed 318.1.

Example 5

Preparing [N-(tert-butoxycarbonyl)-N-methoxy]pentafluoro-phenyl-acetate (5)

[N-(tert-Butoxycarbonyl)-N-methoxy]pentafluoro-phenyl-acetate (5) was prepared as follows: Hydrogen was bubbled through a solution of (4) (7.0 g, 23.7 mmol) containing 5% Pd—$BaSO_4$ (10 mol %) in ethanol (10 mL). After ninety minutes, TLC analysis revealed the disappearance of the starting material. The reaction mixture was diluted with MeOH (20 mL) and filtered through celite to remove catalyst. The solvent was removed under reduced pressure to furnish the pure [N-(tert-Butoxycarbonyl)-N-methoxy]amino acetic acid (4.86 g, 100%). $R_f$=0.12 (20% EtOAc/petroleum ether); $^1H$ δ ($CDCl_3$): 10.84 (broad, 1H), 4.14 (s, 2H), 3.64 (s, 3H), 1.41 (s, 9H); $^{13}C$ δ 173.4, 156.4, 82.3, 62.4, 60.0, 27.8; Electrospray ionization-MS m/z $[M-H]^-$ calculated for $C_8H_{14}NO_5$, 203.99; observed 203.99.

Pentafluorophenol (6.8 g, 37.1 mmol) and diisopropyl carbodiimide (5.8 g, 46.4 mmol) was added to a 0° C. solution of [N-(tert-Butoxycarbonyl)-N-methoxy]amino acetic acid (4.8 g, 23.2 mmol) in $CH_2Cl_2$/dioxane (1:1). The resulting reaction mixture was stirred at room temperature for 16 h, then diluted with $CH_2Cl_2$ (50 mL) and filtered through celite. The filtrate was concentrated in vacuo and the crude residue was purified by flash chromatography (10% EtOAc/Hexanes) to furnish pure product (5) (6.75 g, 78%). $R_f$=0.62 (20% EtOAc/Hexanes); $^1H$ δ ($CDCl_3$): 4.49 (s, 2H), 3.74 (s, 3H), 1.46 (s, 9H); $^{13}C$ δ 164.9, 156.0, 142.2, 139.7, 139.6, 136.5, 82.7, 62.8, 50.9, 27.8; Electrospray ionization-MS m/z $[M+H]^+$ calculated for $C_{14}H_{15}F_5NO_5$, 372.0; observed 372.0.

Example 6

Synthesis of 19-N-methoxyamino-colchicine (8)

19-N-methoxyamino-colchicine (8) was prepared as follows: a mixture of deacetyl colchicine (6) (2.0 g, 5.6 mmol) and activated ester (5) (2.5 g, 6.7 mmol) in $CH_2Cl_2$ (40 mL) was stirred at room temperature for twenty hours. The reaction mixture was concentrated under reduced pressure and the crude material was purified by flash chromatography (8% MeOH/CHCl$_3$) to furnish the pure product (7) as a fluffy yellow solid (3.0 g, 98%). R$_f$=0.53 (8% MeOH/CHCl$_3$) $^1$H δ (CDCl$_3$): 7.40 (s, 1H), 7.35 (d, 1H, 6.8), 7.30 (d, 1H, 10.8), 6.85 (d, 1H, 10.8), 6.48 (s, 1H), 4.61 (apparent ddd, 1H, 11.6, 6.8, 6.2) 4.128 (d, 2H, 4.0), 3.90 (s, 3H), 3.87 (s, 3H), 3.84 (s, 3H), 3.64 (s, 3H), 3.56 (s, 3H), 2.50-2.45 (1H), 2.36-2.28 (1H), 2.23 (1H), 1.87-1.79 (1H), 1.42 (s, 9H); $^{13}$C δ 179.1, 168.1, 163.8, 156.2, 153.4, 151.5, 150.9, 141.4, 136.6, 135.6, 133.9, 130.3, 125.2, 112.8, 107.1, 82.6, 62.1, 61.3, 61.1, 56.1, 55.8, 52.4, 52.2, 36.5, 29.5, 27.9; Electrospray ionization-MS m/z [M+H]$^+$ calculated for C$_{28}$H$_{37}$N$_2$O$_9$, 545.2; observed 545.2.

Trifluoroacetic acid (75 mL, excess) was added to a stirred solution of 19-[N-(tert-Butoxycarbonyl)-N-methoxy]amino-colchicine (7) (3.0 g, 5.5 mmol) in MeOH (10 mL) over a period of two days. After stirring for an additional twenty-four hours the TLC analysis indicated the completion of the reaction. The reaction mixture was concentrated under reduced pressure, and diluted with saturated aq. citric acid solution (50 mL) and neutralized with 1 M aq. NaOH solution at 0° C. to pH=10. The aqueous layer was extracted with CH$_2$Cl$_2$ (4×, 100 mL), the combined organic layers were dried over Na$_2$SO$_4$ and concentrated in vacuo. The crude residue was purified by flash chromatography (8% MeOH/CHCl$_3$) to furnish a yellow solid, 19-N-methoxyamino-colchicine (8) (1.8 g, 73%). R$_f$=0.33 (8% MeOH/CHCl$_3$); $^1$H δ (CDCl$_3$): 7.76 (broad, 1H), 7.41 (s, 1H), 7.27 (d, 1H, 10.0), 6.80 (d, 1H, 10.8), 6.50 (s, 1H), 4.67 (m, 1H), 3.95 (s, 3H), 3.90 (s, 3H), 3.86 (s, 3H), 3.62 (s, 3H), 3.60-3.43 (3H), 3.49 (s, 3H), 2.52-2.47 (1H), 2.42-2.33 (1H), 2.29-2.20 (1H), 1.89-1.82 (1H); $^{13}$C δ 179.3, 169.7, 163.9, 153.3, 151.1, 151.1, 141.5, 136.2, 135.1, 134.0, 130.7, 125.5, 112.3, 107.2, 61.7, 61.4, 61.2, 56.2, 56.0, 54.3, 51.8, 36.7, 29.7; Electrospray ionization-MS m/z [M+H]$^+$ calculated for C$_{23}$H$_{29}$N$_2$O$_7$, 445.2 observed 445.2.

Example 7

Preparing 19-(N-methoxyamino-N-D-glucosyl)colchicine (Col0)

19-(N-methoxyamino-N-D-glucosyl)colchicine (Col0) was prepared as follows: 19-N-methoxyamino-colchicine (8) (33 mg, 74.2 μmol) and D-glucose (27 mg, 150 μmol) in DMF/AcOH (3:1, 820 μL) were stirred at 40° C. for twenty-four hours. The reaction mixture upon concentration furnished the crude colchicine neoglucoside, which was determined by $^1$H NMR to be an isomeric mixture of β:α=87:13. The crude material was filtered through a plug of flash silica to remove traces of unreacted starting materials to furnish the pure material (30 mg, 65%). R$_f$=0.53 (20% MeOH/CHCl$_3$); $^1$H δ (DMSO-d$_6$): 8.54 (d, 0.9H, 7.2), 8.24 (d, 0.1H, 5.2H), 7.22 (s, 1H), 7.12 (d, 1H, 10.8), 7.03 (d, 1H, 11.2), 6.78 (s, 1H), 5.15 (d, 0.1H, 5.2), 5.10 (d, 0.1H, 8.4), 5.05 (d, 0.1H, 5.6), 4.98 (d, 0.9H, 4.4), 4.95 (d, 0.9H, 5.2), 4.84 (d, 0.9H, 3.6), 4.46-4.40 (2H), 3.99 (d, 1H, 8.4), 3.90 (s, 3H), 3.87 (s, 3H), 3.84 (s, 3H), 3.66 (broad dd, 1.4H, 4.4, 4.8), 3.61-3.60 (0.6H), 3.55 (s, 3H), 3.22-3.15 (2H), 3.09-3.02 (2H), 2.61 (dd, 1H, 6.4, 6.0), 2.29-2.20 (1H), 2.08-1.90 (2H); $^1$H δ (500 MHz, 1:1 DMSO-d$_6$:D$_2$O): 7.29 (s, 1H), 7.26 (d, 1H, 6.5), 7.15 (d, 1H, 11.5), 6.74 (s, 1H), 4.35 (dd, 1H, 6.0, 11.5), 6.74 (s, 1H), 4.35 (dd, 1H, 6.0, 11.5), 4.02 (d, 1H, 8.0), 3.85 (s, 3H), 3.77 (s, 3H), 3.74 (s, 3H), 3.67 (bd, 1H, 12.0), 3.58 (bd, 1H, 16.0), 3.50-3.46 (2H), 3.48 (s, 3H), 3.43 (s, 3H), 3.31-3.25 (2H), 3.18-3.09 (2H), 2.58-2.56 (1H), 2.16-2.07 (2H), 1.96-1.92 (1H); $^{13}$C δ (100 MHz, DMSO-d$_6$): 177.9, 168.5, 163.52, 152.9, 150.4, 150.38, 140.7, 135.1, 134.4, 134.2, 130.7, 125.4, 112.1, 107.7, 93.0, 78.5, 77.6, 70.1, 69.9, 61.2, 61.1, 60.8, 60.7, 56.1, 56.0, 55.8, 51.3, 35.6, 29.2; $^1$H, $^{13}$C, gCOSY, gDQCOSY, and gHSQC spectra are shown in FIGS. 4-12 further confirming the identification of the compounds. For simplification of certain $^1$H NMR experiments, D$_2$O was added as a co-solvent to eliminate coupling to sugar hydroxyl groups. Electrospray ionization-MS m/z [M+Na]$^+$ calculated for C$_{29}$H$_{38}$N$_2$O$_{12}$Na, 629.2; observed 629.2. HRMS: calcd for C$_{29}$H$_{38}$N$_2$O$_{12}$Na, 629.23170; observed 629.23224.

Example 8

Preparing 19-(N-methoxyamino-N-22-deoxy-D-ribosyl)colchicine (Col21)

19-(N-METHOXYAMINO-N-22-DEOXY-D-RIBOSYL)COLCHICINE (COL21) was prepared from 19-N-methoxyamino-colchicine (8) (118 mg, 0.26 mmol) and 2-deoxy-D-ribose (72 mg, 0.53 mmol) following a procedure identical to the preparation of Col0 [116 mg, 78%, 81:19 isomeric purity by LC-MS] R$_f$=0.64 (16% MeOH/CHCl$_3$); $^1$H δ (500 MHz, DMSO-d$_6$): 9.56 (d, 0.1H, 7.5), 8.64 (bt, 0.3H, 6.2), 8.59 (t, 0.6H, 8.0), 7.20 (s, 0.3H), 7.19 (s, 0.3H), 7.189 (s, 0.4H), 7.11 (bd, 1H, 10.5), 7.02 (d, 1H, 11.0), 6.76 (s, 1H), 6.26-6.21 (0.1H), 5.34 (d, 0.1H, 4.8), 5.0 (dd, 0.2H, 9.0, 5.0), 4.90-4.83 (0.4H), 4.69 (d, 0.3H, 6.1), 4.66-4.60 (0.5H), 4.57 (t, 0.1H, 5.5), 4.42-4.35 (1.2H), 4.31-4.28 (0.1H), 4.17 (bd, 0.3H, 11.1), 4.10-4.05 (0.2H), 4.02-3.97 (0.2H), 3.95 (b, 0.3H), 3.88 (s, 3H), 3.85 (s, 3H), 3.80 (s, 3H), 3.56 (s, 3H), 3.52-3.47 (2H), 3.43-3.38 (4H), 3.37 (s, 3H), 2.60-2.57 (0.9H), 2.30-2.19 (1.1H), 2.04-1.90 (2.3H), 1.84-1.70 (1.3H), 1.65-1.62 (0.4H); $^1$H δ (500 MHz, DMSO-d$_6$: D$_2$O): 7.20 (bs, 1H), 7.18 (d, 0.9H, 10.9), 7.07 (d, 0.9H, 10.6), 7.04 (d, 0.1H, 4.5), 7.00 (d, 0.1H, 4.0), 6.71 (s, 1H), 6.19 (dd, 0.1H, 15.8, 8.0), 6.10 (bt, 0.1H, 6.0), 4.82 (t, 0.2H, 6.5), 4.76 (t, 0.1H, 6.0), 4.38 (bd, 0.3H, 10), 4.31 (bdd, 1.2H, 13.0, 6.5), 4.04-3.94 (1H), 3.84 (s, 3H), 3.77 (s, 3H), 3.74 (s, 3H), 3.67-3.61 (0.9H), 3.58-3.52 (1.4H), 3.49 (s, 3H), 3.47-3.42 (1.4H), 3.40-3.28 (4.3H, includes OMe), 2.56-2.52 (0.9H), 2.31-2.23 (0.2H), 2.16-2.09 (1H), 2.06-1.98 (1H), 1.96-1.89 (1.3H), 1.82-1.61 (1.6H); $^{13}$C δ (125 MHz, DMSO-d$_6$): 194.3, 177.9, 168.3, 168.2, 168.1, 163.5, 159.8, 152.9, 150.4, 150.5, 140.7, 135.2, 134.3, 134.2, 130.7, 130.6, 130.5, 125.5, 112.1, 107.7, 94.2, 93.1, 89.7, 87.1, 86.4, 86.0, 79.2, 71.2, 70.7, 70.1, 68.3, 68.1, 66.9, 66.3, 64.9, 64.8, 62.4, 61.7, 61.6, 61.1, 61.08, 60.8, 60.7, 56.5, 56.0, 55.8, 55.3, 51.4, 51.3, 36.8, 36.1, 35.5, 34.2, 31.9, 29.2, 21.2; Electrospray ionization-MS m/z [M+H]$^+$ calculated for C$_{28}$H$_{37}$N$_2$O$_{10}$, 561.2; observed 561.2.

Example 9

General Procedure for Neoglyoside Library Synthesis and Purification

A mixture of 19-N-methoxyamino-colchicine (8) (~34 μmol) and appropriate sugar (2.0 eq.), in DMF/AcOH (3:1, 90-100 mM 19-N-methoxyamino-colchicine (8) final concentration) was added in 4 mL glass vials equipped with magnetic stirrer fleas. The reaction mixtures were stirred at 40° C. for twenty-four hours utilizing a forty-eight well reaction block stirplate equipped with a contact thermometer for temperature control. Following removal of the solvent via Speed-Vac (55° C., 3-4 h), 8% MeOH/CHCl$_3$ (0.5-1 mL) was added to the crude reaction mixtures and vortexed for 45-60 seconds. The crude suspended library members were purified with one gram Alltech silica solid phase extraction disposable columns (W.R. Grace & Co., Columbia, Md.) eluting first with 8% MeOH/CHCl$_3$ to first remove any remaining aglycon, followed by elution of library members with 16% MeOH/CHCl$_3$. Following removal of solvent by speed vac, the library members were dried under vacuum to furnish pure neoglycoside products. The stock solutions of neoglycosides in DMSO (20 mM) were prepared and these stock solutions were further diluted to 0.1 mM in MeOH and were characterized by LC-MS utilizing reverse phase HPLC (3×150 mm Phenomenex Luna C18 Column, 2 μL injection, flow rate 0.8 mL/min, linear gradient 20-80% CH$_3$CN/H$_2$O containing 0.1% formic acid, 5%/min gradient over twenty-five minutes) and electrospray ionization. Purity and isomeric ratio of the library members were determined by division of the sum of peak areas with desired neoglycoside mass that were observed at 350 nm/245 nm to the total area of all peaks [210-700 nm]. The average purity of the library was 96.2% and the average isomeric ratio was 81:19. A tabular description of calculated and observed mass, purity, isomeric ratio for all library members is provided in Table 2.

TABLE 2

LCMS information for colchicine-neoglycoside library.

| Neoglycoside | Calculated Mass | Observed Mass | Percent purity | LC-MS-Peak ratio |
|---|---|---|---|---|
| D-lyxoside (Col1) | 576.2 | 576.2 | 100 | 78:22 |
| 6-deoxy-D-glucoside (Col2) | 590.2 | 590.2 | 100 | 80:20 |
| 3-deoxy-D-glucoside (Col3) | 590.2 | 590.2 | 100 | 81:19 |
| D-xyloside (Col4) | 576.2 | 576.2 | 100 | 81:19 |
| D-riboside (Col5) | 576.2 | 576.2 | 100 | 82:18 |
| 2-deoxy-D-galactoside (Col6) | 590.2 | 590.2 | 100 | 76:24 |
| L-lyxoside (Col7) | 576.2 | 576.2 | 100 | 88:12 |
| L-glucoside (Col8) | 606.2 | 606.2 | 100 | 86:14 |
| D-fucoside (Col 9) | 590.2 | 590.2 | 100 | 88:12 |
| L-mannoside (Col10) | 606.2 | 606.2 | 100 | 87:13 |
| D-alloside (Col11) | 606.2 | 606.2 | 100 | 81:19 |
| L-galactoside (Col12) | 606.2 | 606.2 | 100 | 76:24 |
| maltotrioside (Col13) | 930.3 | 930.3 | 100 | 79:21 |
| L-fucoside (Col14) | 590.2 | 590.2 | 100 | 86:14 |
| D-glucuronoside (Col15) | 620.2 | 620.2 | 100 | 88:12 |
| 2-deoxy-D-glucoside (Col16) | 590.2 | 590.2 | 100 | 84:16 |
| L-xyloside (Col17) | 576.2 | 576.2 | 100 | 84:16 |
| D-Galacturonoside (Col18) | 620.2 | 620.2 | 76 | 100:0 |
| 2-deoxy-L-riboside (Col19) | 560.2 | 560.2 | 100 | 71:19 |
| D-arabinoside (Col20) | 576.2 | 576.2 | 100 | 80:20 |
| 2-deoxy-D-riboside (Col21) | 560.2 | 560.2 | 88 | 81:19 |
| L-riboside (Col22) | 576.2 | 576.2 | 100 | 83:17 |
| D-melibioside (Col23) | 768.3 | XXXXXX | XXXXX | XXXXX |
| D-altroside (Col24) | 606.2 | 606.2 | 100 | 81:19 |
| L-arabinoside (Col25) | 576.2 | 576.2 | 100 | 81:19 |
| D-mannoside (Col27) | 606.2 | 606.2 | 100 | 73:27 |
| N-acetyl-D-galactosaminoside (Col28) | 647.2 | 647.2 | 100 | 73:27 |
| novioside (Col29) | 618.3 | 618.3 | 100 | 76:24 |
| L-alloside (Col30) | 606.2 | 606.2 | 100 | 77:23 |
| D-taloside (Col31) | 606.2 | 606.2 | 100 | 78:22 |
| L-altroside (Col32) | 606.2 | 606.2 | 100 | 78:22 |
| 3-fluoro-3-deoxy-D-glucoside (Col33) | 608.2 | 608.2 | 53 | 84:16 |
| 2-fluoro-2-deoxy-D-glucoside (Col34) | 608.2 | 608.2 | 62 | 58:42 |
| N-acetyl-D-mannosaminoside (Col35) | 647.2 | 647.2 | 92 | 76:24 |
| D-lactoside (Col36) | 768.3 | XXXXXX | XXXXX | XXXXXX |
| L-rhamnoside (Col37) | 590.3 | 590.3 | 100 | 92:8 |
| D-maltoside (Col38) | 768.3 | 768.3 | trace | product |
| N-acetyl-D-glucosaminoside (Col39) | 647.3 | XXXX | XXXX | XXXX |
| D-cellobioside (Col40) | 768.8 | XXXX | XXXX | XXXX |
| 6-deoxy-6-chloro-D-galactoside (Col41) | 624.2 | 624.1 | 100 | 88:12 |
| 6-deoxy-6-bromo-D-galactoside (Col42) | 668.1 | 668.1 | 100 | 81:19 |
| 6-deoxy-6-azido-D-galactoside (Col43) | 631.2 | 631.2 | 100 | 81:19 |
| 4-deoxy-4-azido-D-glucoside (Col44) | 631.2 | 631.2 | 25 | 100:0 |
| D-glucorono-6,3-lactonide (Col45) | 602.2 | 602.1 | >94 | 89:11 |
| 2-deoxy-2-amino-D-glucoside (Col46) | 642.1 | XXXXX | XXXX | XXXXX |
| 3-O-methyl-D-glucoside (Col47) | 620.2 | 620.2 | 100 | 70:30 |
| 2,3,4-tri-O-acetyl-L-rhamnoside (Col48) | 716.28 | XXXXX | XXXX | XXXX |
| mycaroside (Col49) | 588.3 | 588.3 | 93 | 87:13 |
| 2,3,4,6-tetra-O-benzyl-D-glucopyranoside (Col50) | 966.4 | XXXXX | XXXX | XXXXX |
| 2,3,4-tri-O-benzyl-L-fucopyranoside (Col51) | 861.0 | XXXXX | XXXX | XXXXX |
| 2,3,5-tri-O-benzyl-D-arabinofuranoside (Col52) | 846.9 | XXXX | XXXX | XXXX |
| 2,3,5-tri-O-benzyl-D-ribofuranoside (Col53) | 846.4 | 846.4 | 100 | 81:19 |
| 6-deoxy-6-fluoro-D-glucoside (Col54) | 608.2 | 602.2 | 100 | 84:16 |
| 4-O-(β-D-galacto pyranosyl-D-mannopyranoside) (Col55) | 768.3 | XXXXX | XXXXX | XXXX |
| 6-deoxy-6-acyl-D-galactoside (Col56) | 618.2 | 618.2 | 100 | 70:30 |
| L-taloside (Col57) | 606.2 | 606.2 | 100 | 83:17 |
| 6-thio-D-mannose dimer (Col58) | 816.2 | 816.2 | 100 | 88:12 |
| 6-deoxy-6-N-decanoyl-D-glucosaminoside (Col59) | 759.4 | 759.4 | 100 | 100:0 |
| 3-deoxy-3-N-decanoyl-D-glucosaminoside (Col60) | 759.4 | 759.4 | 100 | 100:0 |

TABLE 2-continued

LCMS information for colchicine-neoglycoside library.

| Neoglycoside | Calculated Mass | Observed Mass | Percent purity | LC-MS-Peak ratio |
|---|---|---|---|---|
| 3-deoxy-3-carbamic acid allyl ester-D-glucoside (Col61) | 689.3 | 689.3 | 100 | 87:13 |
| 6-deoxy-3-carbamic acid allyl ester-D-glucoside (Col62) | 689.3 | 689.3 | 100 | 53:47 |
| 2,3,4,6-tetra-O-benzyl-D-mannopyranoside (Col63) | 967.1 | XXXXX | XXXX | XXXX |
| 3-deoxy-3-azido-D-glucoside (Col64) | 631.6 | 632.2 | XXXX | XXXX |
| D-Digitoxoside (Col65) | 574.2 | 574.3 | 100 | 86:14 |
| 6-deoxy-6-amino-D-glucoside (Col66) | 605.6 | 606.2 | XXXX | XXXX |
| D-galactoside (Col67) | 606.2 | 606.2 | 100 | 66:34 |
| 6-deoxy-6-thio-acyl-D-galactoside (Col68) | 664.2 | 664.2 | 100 | 91:9 |
| D-idoside (Col69) | 606.2 | 606.2 | 100 | 100:0 |
| L-idoside (Col70) | 606.2 | 606.2 | 100 | 100:0 |
| D-guloside (Col71) | 606.2 | 606.2 | 100 | 74:26 |
| D-glucoside (Col0) | 606.2 | 606.2 | 100 | 72:28 |

TABLE 3

HRMS data for compounds in Table 2.

| Library Member | Formula [M + H]+ | Calculated m/z | Observed m/z |
|---|---|---|---|
| Col 0 | $C_{29}H_{38}N_2O_{12}Na$ | 629.23170 | 629.23224 |
| Col 6 | $C_{29}H_{39}N_2O_{11}$ | 591.25484 | 591.25216 |
| Col45 | $C_{29}H_{35}N_2O_{12}$ | 603.21845 | 603.21605 |
| Col19 | $C_{28}H_{37}N_2O_{10}$ | 561.24427 | 561.24143 |
| Col21 | $C_{28}H_{37}N_2O_{10}$ | 561.24427 | 561.24057 |
| Col56 | $C_{30}H_{39}N_2O_{12}$ | 619.24975 | 619.24712 |
| Col65 | $C_{29}H_{39}N_2O_{10}$ | 575.25992 | 575.25753 |

Example 10

Cytotoxicity Assays

Cytotoxicity assays were preformed to determine the efficacy of the compounds in the neoglycosylated library as cytotoxic agents. The cytotoxicity assays were prepared as follows: all cell lines were maintained as previously reported (Langenhan, J. M.; et al. Proc. Natl. Acad. Sci. U.S.A. 2005, 102, 12305). Cells were harvested by trypsinization using 0.25% trypsin and 0.1% EDTA and then counted in a ViCell XR coulter counter in duplicate, before and after dilution for assay plating. Cell plating, compound handling and assay set up were performed as previously reported (Langenhan, J. M.; et al., Proc. Natl. Acad. Sci. U.S.A. 2005, 102, 12305). Calcein AM (acetoxymethyl ester) reagent (30 µL, 1M) was added and the cells were incubated for 30 min at 37° C. Plates were read for emission by using a fluorescein filter ($\lambda_{ex}$ 485 nm, $\lambda_{em}$ 535 nm). An equal volume (30 µL) of cell titer-glow reagent (Promega Corporation, Inc.) was added and incubated for ten minutes at room temperature with gentle agitation to lyse the cells. Each plate was re-read for luminescence to confirm the inhibition observed in the fluorescent Calcein AM assay. $IC_{50}$ calculations for library members were done by plotting percent inhibitions as a function of log [concentration] and then fit to a four parameter logistic model which allowed for a variable Hill slope utilizing XLfit 4.2 software as previously reported (Langenhan, J. M.; et al., Proc. Natl. Acad. Sci. U.S.A. 2005, 102, 12305).

Fifty-seven library members were tested in a panel of nine human cancer cell lines and one normal mouse control cell line. $IC_{50}$ were determined using a threshold of 10 µM (three orders of magnitude greater than the $IC_{50}$ of the parent molecule colchicine) established as the "non-toxic" cut off. Dose response experiments were performed in triplicate and repeated on a separate day for all compounds below the non-toxic cutoff in each cell line. All fifty-seven library members had an $IC_{50}$ below the non-toxic cutoff in at least one cell line. Fifteen library members had an $IC_{50}$ of less than 1 µM and were further tested in secondary assays to determine the mechanism of action. Library member Col53 was excluded from further analysis due to precipitation in cell culture media. All cytotoxicity screen data is presented in Table 4. It is important to note that these data show that, in many cases, the colchicines neoglycoside behaved neither as a pure calchicine, pure taxane or a pure anthracyline but rather had intermediate effects. Further, the colchicines neoglycosides were still cytotoxic indicating their efficacy as a therapeutic agent.

TABLE 4

Cytotoxicity data for all colchicine neoglycosides and relevant standards (in µM with % error in parentheses).

| | | Col1 | Col2 | Col3 | Col4 | Col5 | Col6 | Col7 | Col8 |
|---|---|---|---|---|---|---|---|---|---|
| Du145 | calcein | 2.00 | >7.79 | 6.56 | >10 | 6.78 | 0.958 (0.164) | 4.73 | >10 |
| | CTG | 1.97 | >10 | >10 | >10 | >10 | 0.892 (0.084) | >10 | >10 |
| HCT-116 | calcein | 0.71 | >6.01 | 1.55 | 9.89 | 7.57 | 0.792 (0.156) | 1.06 | >0.30 |
| | CTG | 3.13 | >9.56 | 5.00 | >10 | 9.81 | 0.624 (0.060) | 5.08 | >5.0 |
| Hep 3B | calcein | 3.69 | >10 | 4.07 | >3.35 | 6.52 | 1.124 (0.181) | 4.74 | >10 |
| | CTG | 3.50 | >10 | 5.16 | >10 | 9.86 | 0.817 (0.072) | 4.89 | >10 |
| SF-268 | calcein | 4.00 | >10 | 8.42 | 8.93 | 4.59 | 0.691 (0.150) | 4.90 | >10 |
| | CTG | 3.86 | 8.43 | 5.32 | 8.26 | 5.01 | 0.632 (0.042) | 4.97 | >10 |
| SK-OV-3 | calcein | 4.00 | >10 | 4.21 | >10 | >10 | 0.381 (0.054) | 5.04 | >10 |
| | CTG | 4.00 | 9.86 | 4.42 | >10 | >10 | 0.388 (0.116) | >10 | >10 |
| NCI/ADR | calcein | 1.91 | >10 | >10 | >10 | 5.06 | 0.887 (0.173) | >10 | >10 |
| RES | CTG | 2.63 | >10 | >10 | >10 | 4.84 | 0.877 (0.069) | >10 | >10 |

TABLE 4-continued

Cytotoxicity data for all colchicine neoglycosides and relevant standards (in μM with % error in parentheses).

| | | | | | | | | |
|---|---|---|---|---|---|---|---|---|
| NCI-H460 | calcein | 3.93 | 5.42 | 1.96 | >10 | 5.76 | 0.948 (0.128) | 5.69 | >9.8 |
| | CTG | 4.51 | 7.24 | 8.37 | >10 | 5.06 | 0.745 (0.053) | 7.08 | >10 |
| MCF7 | calcein | 1.33 | 4.77 | >10 | >10 | 2.88 | 2.215 (0.340) | 3.99 | >8.03 |
| | CTG | 1.90 | 4.86 | 3.25 | >10 | 2.84 | 0.665 (0.063) | 2.65 | >5.81 |
| A549 | calcein | 1.21 | 7.94 | >10 | >10 | >10 | 0.942 (0.192) | 9.76 | >10 |
| | CTG | 2.91 | 8.78 | 9.91 | >10 | >10 | 0.782 (0.055) | >10 | >10 |
| NmuMG | calcein | 6.49 | >10 | >10 | >10 | >10 | 4.173 (0.588) | >10 | >10 |
| | CTG | >10 | >10 | >10 | >10 | >10 | 3.261 | >10 | >10 |

| | | Col9 | Col10 | Col11 | Col12 | Col13 | Col14 | Col15 | Col16 |
|---|---|---|---|---|---|---|---|---|---|
| Du145 | calcein | >9.14 | 6.97 | >10 | 5.20 | >10 | >10 | 1.64 | 0.910 |
| | CTG | >10 | 5.32 | >10 | 5.66 | >10 | >10 | 1.27 | 0.705 |
| HCT-116 | calcein | >10 | 1.80 | >10 | 7.87 | >10 | 6.22 | 0.70 | 0.947 |
| | CTG | >9.44 | 4.53 | >10 | 5.24 | >10 | 6.21 | 1.03 | 0.648 |
| Hep 3B | calcein | >10 | >10 | >10 | >10 | >10 | >10 | 3.44 | 1.439 |
| | CTG | >10 | 7.81 | >10 | >10 | >10 | >10 | 3.28 | 1.915 |
| SF-268 | calcein | >10 | 2.71 | >10 | 5.14 | >10 | 9.89 | 1.02 | 1.544 |
| | CTG | >10 | 5.00 | >10 | 5.25 | >10 | 5.28 | 1.17 | 1.068 |
| SK-OV-3 | calcein | >7.83 | >10 | >10 | >10 | >10 | >10 | 2.88 | 0.625 |
| | CTG | >10 | 5.16 | >10 | >10 | >10 | >10 | 1.07 | 0.432 |
| NCI/ADR RES | calcein | >10 | 9.49 | >10 | 9.17 | >10 | >10 | 1.54 | 0.899 |
| | CTG | >10 | 8.122 | >10 | 9.42 | >10 | >10 | 1.66 | 1.675 |
| NCI-H460 | calcein | >10 | 5.34 | >10 | >10 | 2.58 | >10 | 0.96 | 0.808 |
| | CTG | >10 | 4.55 | 6.69 | 9.53 | >10 | 9.03 | 1.08 | 0.946 |
| MCF7 | calcein | >8.75 | 6.90 | >10 | 6.97 | >10 | >10 | 4.41 | 1.921 |
| | CTG | >9.96 | 6.565 | >10 | 7.8 | 9.86 | 4.95 | 0.99 | 2.653 |
| A549 | calcein | >10 | >10 | >10 | >10 | >10 | >10 | 3.92 | 1.682 |
| | CTG | >10 | 6.08 | >10 | >10 | >10 | >10 | 2.21 | 3.903 |
| NmuMG | calcein | >10 | >10 | >10 | >10 | >10 | >10 | >5 | 4.415 |
| | CTG | >10 | >10 | >10 | >10 | >10 | >10 | >5 | 1.610 |

| | | Col17 | Col18 | Col19 | Col20 | Col21 | Col22 | Col24 | Col25 |
|---|---|---|---|---|---|---|---|---|---|
| Du145 | calcein AM | >10 | 1.187 (0.204) | 0.262 (0.064) | 3.74 | 0.294 (0.053) | >10 | >10 | >10 |
| | CTG | 8.48 | 1.125 (0.077) | 0.369 (0.049) | 2.41 | 0.344 (0.044) | 2.38 | >10 | 7.40 |
| HCT-116 | calcein AM | 7.35 | 0.865 (0.097) | 0.431 (0.070) | 5.00 | 0.344 (0.078) | 2.09 | >10 | 2.95 |
| | CTG | 5.48 | 0.886 (0.064) | 0.299 (0.057) | 4.90 | 0.444 (0.138) | 1.54 | >10 | 2.09 |
| Hep 3B | calcein AM | >10 | 2.269 (0.199) | 0.437 (0.078) | >10 | 1.291 (0.186) | 3.95 | >10 | >10 |
| | CTG | >10 | 2.004 (0.117) | 0.376 (0.036) | >10 | 0.633 (0.198) | 2.44 | >10 | >10 |
| SF-268 | calcein AM | 9.72 | 1.107 (0.135) | 0.575 (0.097) | 3.95 | 0.349 (0.080) | 4.86 | >10 | 4.46 |
| | CTG | 5.93 | 0.834 (0.044) | 0.284 (0.026) | 2.54 | 0.206 (0.017) | 4.16 | >10 | 6.80 |
| SK-OV-3 | calcein AM | >10 | 1.072 (0.148) | 0.538 (0.123) | >10 | 0.296 (0.040) | 4.84 | >10 | 2.51 |
| | CTG | >10 | 1.083 (0.063) | 0.240 (0.035) | >10 | 0.362 (0.034) | 4.84 | >10 | 8.51 |
| NCI/ADR RES | calcein AM | >10 | 0.828 (0.098) | 0.315 (0.037) | 7.74 | 0.209 (0.048) | 3.56 | >10 | 5.53 |
| | CTG | >10 | 1.110 (0.074) | 0.359 (0.033) | 7.846 | 0.333 (0.055) | 2.23 | >10 | 5.14 |
| NCI-H460 | calcein AM | 5.61 | 1.130 (0.115) | 0.191 (0.029) | 3.71 | 0.355 (0.042) | 2.00 | >10 | 5.78 |
| | CTG | 5.17 | 0.993 (0.061) | 0.415 (0.045) | 5.21 | 0.313 (0.013) | 1.16 | >10 | 4.41 |
| MCF7 | calcein AM | 5.09 | 1.493 (0.134) | 2.823 (0.328)$^2$ | 2.35 | 0.609 (0.168) | 2.87 | >10 | 3.43 |
| | CTG | 6.22 | 1.163 (0.076) | 0.916 (0.157) | 4.44 | 0.514 (0.097) | 4.27 | >10 | 3.02 |
| A549 | calcein AM | >10 | 1.074 (0.189) | 0.636 (0.117) | >10 | 0.248 (0.054) | 9.44 | >10 | 5.26 |
| | CTG | 9.40 | 1.103 (0.076) | 0.376 (0.053) | 9.07 | 0.286 (0.027) | 4.22 | >10 | 5.02 |
| NmuMG | calcein AM | >10 | 2.615 (0.322)$^2$ | 2.847 (0.436) | >10 | 0.507 (0.071) | >10 | >10 | >10 |
| | CTG | >10 | 2.087 (0.226)$^2$ | 2.907 (0.381) | >10 | 0.415 (0.048) | >10 | >10 | 5.70 |

| | | Col27 | Col28 | Col29 | Col30 | Col31 | Col32 | Col33 | Col34 |
|---|---|---|---|---|---|---|---|---|---|
| Du145 | calcein AM | >10 | >10 | 0.55 | >10 | 3.20 | >10 | 5.44 | 0.328 (0.064) |
| | CTG | >10 | >10 | 1.24 | >10 | 3.07 | >10 | 9.60 | 0.142 (0.018) |
| HCT-116 | calcein AM | 2.64 | 2.11 | 1.01 | 2.71 | 1.58 | 2.27 | 0.65 | 0.293 (0.050) |
| | CTG | 2.51 | 5.10 | 1.05 | 2.08 | 3.27 | 2.22 | 1.46 | 0.172 (0.012) |
| Hep 3B | calcein AM | 3.88 | >10 | 2.94 | >10 | >10 | >10 | 1.99 | 1.174 (0.249) |
| | CTG | >10 | >0 | 2.47 | >10 | >10 | >10 | 2.67 | 0.545 (0.106) |
| SF-268 | calcein AM | 4.00 | 3.56 | 1.28 | 5.24 | 3.62 | 4.41 | 2.33 | 0.452 (0.081) |
| | CTG | 2.50 | 5.70 | 1.12 | >10 | 7.14 | 2.58 | 0.86 | 0.281 (0.021) |
| SK-OV-3 | calcein AM | 3.07 | 7.32 | 4.35 | >10 | 3.58 | 6.30 | 1.89 | 0.800 (0.609) |
| | CTG | 7.38 | 5.18 | 1.03 | >10 | 6.19 | 7.28 | 1.25 | 0.325 (0.048) |
| NCI/ADR RES | calcein AM | 3.89 | >10 | 1.18 | 7.17 | 3.63 | 1.04 | >10 | >1 |
| | CTG | 2.70 | 9.95 | 1.56 | >10 | 4.83 | 8.39 | >10 | >1 |
| NCI-H460 | calcein AM | 3.77 | >10 | 3.37 | >10 | 2.09 | 1.92 | >10 | >1 |
| | CTG | 2.55 | 9.76 | 0.98 | >10 | 4.59 | 1.14 | 4.39 | >1 |
| MCF7 | calcein AM | 1.51 | 6.67 | 0.30 | >10 | 0.39 | 6.65 | 6.13 | 0.254 (0.057) |
| | CTG | 1.70 | 4.87 | 0.61 | >10 | 2.00 | 4.37 | 6.64 | 0.242 (0.045) |
| A549 | calcein AM | 5.84 | >10 | 2.18 | >10 | 4.12 | 2.89 | 1.87 | 0.778 (0.086) |
| | CTG | 4.69 | >10 | 1.86 | >10 | 8.04 | 5.33 | 2.02 | 0.545 (0.059) |
| NmuMG | calcein AM | 2.90 | 9.57 | >5 | >10 | >10 | >10 | >10 | 0.760 (0.241) |
| | CTG | 3.17 | >10 | >5 | >10 | >10 | >10 | 5.93 | 0.451 (0.143) |

TABLE 4-continued

Cytotoxicity data for all colchicine neoglycosides and relevant standards (in μM with % error in parentheses).

| | | Col35 | Col37 | Col38 | Col41 | Col42 | Col43 | Col44 | Col45 |
|---|---|---|---|---|---|---|---|---|---|
| Du145 | calcein | >10 | 4.36 | 0.342 | 6.74 | 4.26 | 4.19 | >1 | 0.939 |
| | CTG | 5.26 | 5.81 | 0.215 | 6.69 | 4.47 | 4.87 | >1 | 1.143 |
| HCT-116 | calcein | 4.51 | 4.31 | 0.307 | 4.94 | 4.00 | >10 | 0.389 | 0.529 |
| | CTG | 4.87 | 4.53 | 0.354 | 4.90 | 4.87 | 9.97 | 0.588 | 0.834 |
| Hep 3B | calcein | >5 | 9.57 | 1.387 | 5.99 | >10 | 3.89 | 0.671 | 0.962 |
| | CTG | >5 | 8.26 | 0.229 | 8.80 | >10 | 5.30 | 0.453 | 0.793 |
| SF-268 | calcein | 5.02 | 4.68 | 0.319 | 7.87 | 3.31 | 8.46 | 0.412 | 0.462 |
| | CTG | 5.28 | 4.79 | 0.160 | 6.93 | 6.37 | 5.15 | 0.229 | 0.398 |
| SK-OV-3 | calcein | 1.37 | >10 | 0.316 | 7.95 | >10 | 5.79 | >1 | 0.887 |
| | CTG | 4.73 | 5.58 | 0.252 | 5.61 | 8.36 | >10 | >1 | 0.836 |
| NCI/ADR | calcein | 6.11 | 4.48 | 0.173 | 3.68 | 2.23 | 2.51 | >1 | 0.403 |
| RES | CTG | 8.46 | 4.56 | 0.199 | 4.97 | 2.49 | 5.04 | >1 | 1.138 |
| NCI-H460 | calcein | 7.12 | 6.70 | 0.487 | 2.31 | >10 | 2.36 | >1 | 1.024 |
| | CTG | 4.83 | 3.72 | 0.112 | 5.48 | 4.40 | 5.01 | >1 | 0.775 |
| MCF7 | calcein | 4.38 | 1.56 | 0.313 | 1.85 | 3.69 | 3.68 | 0.676 | 0.679 |
| | CTG | 2.46 | 3.81 | 0.291 | 3.36 | 4.90 | 4.91 | 0.596 | 0.760 |
| A549 | calcein | 0.75 | 7.28 | 0.508 | 1.07 | 2.64 | >10 | 0.649 | 1.055 |
| | CTG | 0.55 | 7.07 | 0.244 | 3.70 | 3.94 | >10 | 0.315 | 1.100 |
| NmuMG | calcein | >10 | 7.76 | 0.875 | 9.27 | 2.92 | 3.93 | 3.66 (0.805)[2] | >10 |
| | CTG | >10 | 7.72 | 0.976 (0.116) | >10 | 2.83 | 3.82 | 1.425 (0.134) | 1.461 (0.511) |

| | | Col47 | Col49 | Col53 | Col54 | Col56 | Col57 | Col58 | Col59 |
|---|---|---|---|---|---|---|---|---|---|
| Du145 | calcein AM | >10 | 8.56 | 0.032 (0.005) | >10 | 1.094 (0.116) | 4.69 | 2.12 | 7.09 |
| | CTG | 5.22 | 5.20 | 0.041 (0.003) | >10 | 1.146 (0.100) | 4.71 | 2.09 | 5.28 |
| HCT-116 | calcein AM | 2.40 | 7.08 | 0.026 (0.006) | 4.48 | 0.669 (0.178) | 4.23 | 2.51 | 7.42 |
| | CTG | 2.49 | 5.31 | 0.039 (0.005) | 4.74 | 0.761 (0.064) | 3.86 | 1.90 | 5.17 |
| Hep 3B | calcein AM | 5.11 | >10 | 0.069 (0.006) | 4.66 | 2.228 (0.286) | >10 | 5.02 | 7.36 |
| | CTG | 9.61 | 9.76 | 0.047 (0.002) | >10 | 1.479 (0.141) | >10 | 8.62 | 5.70 |
| SF-268 | calcein AM | 5.82 | 7.86 | 0.018 (0.003) | >10 | >1 | 8.12 | 9.09 | 9.44 |
| | CTG | 4.77 | 9.94 | 0.037 (0.004) | >10 | 1.756 (0.146) | 5.28 | 8.013 | 5.53 |
| SK-OV-3 | calcein AM | 4.93 | >10 | 0.036 (0.005) | >10 | 1.182 (0.178) | 10 | 7.56 | 7.11 |
| | CTG | 5.00 | >10 | 0.042 (0.002) | >10 | 0.901 (0.072) | 9.61 | 6.07 | 5.08 |
| NCI/ADR | calcein AM | 6.10 | >10 | 0.037 (0.006) | >10 | 0.994 (0.117) | 4.26 | 1.57 | 7.97 |
| RES | CTG | 5.03 | 5.38 | 0.046 (0.002) | >10 | 1.161 (0.099) | 4.76 | 3.60 | 5.16 |
| NCI-H460 | calcein AM | >10 | 9.31 | 0.071 (0.013) | 4.90 | 1.094 (0.104) | >10 | >10 | 5.21 |
| | CTG | >10 | 10 | 0.041 (0.002) | 3.82 | 1.550 (0.115) | >10 | >10 | 4.95 |
| MCF7 | calcein AM | 2.33 | 5.21 | 0.039 (0.011) | >10 | 0.812 (0.204) | 3.29 | 3.86 | 6.19 |
| | CTG | 1.87 | 4.38 | 0.049 (0.004) | >10 | 3.13 (0.277) | 4.49 | 2.50 | 5.51 |
| A549 | calcein AM | >10 | >10 | 0.062 (0.008) | >10 | 2.094 (0.364) | 4.85 | 4.62 | >10 |
| | CTG | 8.17 | >10 | 0.048 (0.003) | >10 | 1.909 (0.137) | 4.93 | 3.92 | 8.14 |
| NmuMG | calcein AM | >10 | 8.84 | 0.392 (0.083) | >10 | 1.493 (0.241) | 9.87 | >10 | 8.43 |
| | CTG | >10 | >10 | 0.120 (0.021) | >10 | 1.522 (0.228) | 8.31 | 6.39 | >10 |

| | | Col60 | Col61 | Col62 | Col65 | Col67 | Col68 | Col69 | Col70 |
|---|---|---|---|---|---|---|---|---|---|
| Du145 | calcein AM | 6.20 | 7.51 | 9.92 | 0.939 (0.207) | 1.64 | 1.73 | 0.78 | 0.80 |
| | CTG | 4.79 | 7.81 | >10 | 0.850 (0.074) | 1.71 | 4.19 | 1.56 | 2.05 |
| HCT-116 | calcein AM | 6.56 | 5.95 | >10 | 0.897 (0.081) | 1.46 | 3.87 | 1.13 | 1.65 |
| | CTG | 4.68 | 5.05 | 9.68 | 0.918 (0.076) | 1.65 | 3.37 | 1.51 | 2.18 |
| Hep 3B | calcein AM | >10 | >10 | 1.36 | 1.875 (0.219) | 10 | 7.92 | 2.33 | >10 |
| | CTG | 4.97 | 9.10 | 9.99 | 1.698 (0.064) | 7.93 | 5.22 | 3.47 | >10 |
| SF-268 | calcein AM | 4.13 | 7.91 | 5.88 | 0.665 (0.205) | 1.20 | 3.27 | 0.79 | 1.09 |
| | CTG | 5.03 | 5.20 | >10 | 0.800 (0.045) | 1.75 | 3.85 | 1.86 | 1.76 |
| SK-OV-3 | calcein AM | 4.15 | >10 | >10 | 1.031 (0.187) | 2.14 | 2.43 | 1.78 | 1.21 |
| | CTG | 4.38 | 7.99 | >10 | 0.634 (0.035) | 2.15 | 4.50 | 1.73 | 2.69 |
| NCI/ADR | calcein AM | 4.65 | 7.19 | 8.69 | 0.694 (0.167) | 1.30 | 2.04 | 2.06 | 1.56 |
| RES | CTG | 4.98 | 8.23 | >10 | 0.893 (0.048) | 1.99 | 4.88 | 1.71 | 1.64 |
| NCI-H460 | calcein AM | 5.88 | 5.77 | >10 | 0.744 (0.106) | 2.54 | 3.12 | 1.03 | 5.24 |
| | CTG | 3.98 | 5.00 | >10 | 0.862 (0.046) | 1.69 | 4.41 | 1.34 | 0.76 |
| MCF7 | calcein AM | 3.04 | 3.71 | 9.20 | 0.648 (0.134) | 1.84 | 2.54 | 4.02 | 5.67 |
| | CTG | 3.36 | 6.02 | 8.76 | 0.946 (0.038) | 1.40 | 2.42 | 1.22 | 1.43 |
| A549 | calcein AM | >10 | 4.98 | >10 | 2.301 (0.328)[2] | 3.87 | 7.67 | 4.41 | 5.44 |
| | CTG | >10 | >10 | >10 | 1.491 (0.162) | 2.97 | 4.77 | 2.51 | 3.47 |
| NmuMG | calcein AM | 6.04 | >10 | >10 | 3.318 (0.594)[2] | 8.38 | 9.44 | >10 | >10 |
| | CTG | 8.37 | 9.74 | >10 | 7.747 (0.576)[2] | 7.54 | 9.83 | 7.90 | 6.81 |

| | | Col | Col0 | 6 | 7 | 8 | colchin | doxorubi | paclitaxel |
|---|---|---|---|---|---|---|---|---|---|
| Du145 | calcein AM | 4.67 | >10 | 0.084 (0.010) | 0.174 (0.026) | 0.084 (0.010) | 0.022 (0.003) | 0.339 (0.061) | 0.290 (0.132) |
| | CTG | >10 | >10 | 0.064 (0.011) | 0.142 (0.012) | 0.064 (0.011) | 0.169 (0.032) | 0.842 (0.138) | 0.432 (0.189)[2] |
| HCT-116 | calcein AM | 8.02 | 4.84 | 0.098 (0.021) | 0.221 (0.039) | 0.098 (0.021) | 0.091 (0.033) | 0.524 (0.157) | 0.275 (0.200)[2] |

TABLE 4-continued

Cytotoxicity data for all colchicine neoglycosides and relevant standards (in μM with % error in parentheses).

|  |  |  |  |  |  |  |  |  |  |
|---|---|---|---|---|---|---|---|---|---|
|  | CTG | >10 | 9.64 | 0.116 (0.021) | 0.192 (0.023) | 0.116 (0.021) | 0.153 (0.029) | 0.812 (0.102) | 0.168 (0.201)[2] |
| Hep 3B | calcein AM | 9.38 | 5.14 | 0.284 (0.066) | 0.506 (0.104) | 0.284 (0.066) | —[1] | 0.268 (0.039)[2] | 0.166 (0.021) |
|  | CTG | >10 | >10 | 0.141 (0.021) | 0.431 (0.029) | 0.141 (0.021) | 0.329 (0.041)[2] | 0.519 (0.033)[2] | —[1] |
| SF-268 | calcein AM | >10 | 9.70 | 0.191 (0.039) | 0.104 (0.012) | 0.191 (0.039) | 0.035 (0.011)[2] | 0.385 (0.041)[2] | 0.315 (0.076) |
|  | CTG | >10 | 6.15 | 0.116 (0.033) | 0.156 (0.013) | 0.116 (0.033) | 0.067 (0.028)[2] | 0.249 (0.026)[2] | —[1] |
| SK-OV-3 | calcein AM | 7.62 | >10 | 0.316 (0.082) | 0.097 (0.008) | 0.316 (0.082) | 0.024 (0.003)[2] | 0.621 (0.207)[2] | 0.034 (0.011)[2] |
|  | CTG | >10 | >10 | 0.455 (0.071) | 0.184 (0.041) | 0.455 (0.071) | 0.035 (0.008)[2] | 0.394 (0.031)[2] | 0.042 (0.004)[2] |
| NCI/ADR RES | calcein AM | 6.32 | >10 | 0.065 (0.010) | 0.127 (0.013) | 0.065 (0.010) | 0.027 (0.002) | 0.174 (0.041) | 0.043 (0.005)[2] |
|  | CTG | >10 | >10 | 0.079 (0.009) | 0.181 (0.021) | 0.079 (0.009) | 0.018 (0.002) | 0.570 (0.081) | —[1] |
| NCI-H460 | calcein AM | >10 | 8.92 | 0.072 (0.012) | 4.082 (0.412) | 0.072 (0.012) | 0.022 (0.015) | 1.001 (0.164)[2] | 0.105 (0.022) |
|  | CTG | >10 | 4.79 | 0.087 (0.008) | 1.495 (0.465) | 0.087 (0.008) | 0.027 (0.006) | 0.651 (0.120) | 0.053 (0.008) |
| MCF7 | calcein AM | 6.37 | 3.30 | 0.163 (0.036) | 0.128 (0.032) | 0.163 (0.036) | 0.21 (0.04)[2] | 0.240 (0.021) | 0.195 (0.028) |
|  | CTG | 5.15 | 3.94 | 0.072 (0.009) | 0.087 (0.034) | 0.072 (0.009) | 0.221 (0.008)[2] | 0.311 (0.054) | 4.558 (0.340)[2] |
| A549 | calcein AM | >10 | >10 | 0.222/ (0.030) | 0.203 (0.103) | 0.222 (0.030) | 0.118 (0.025) | 0.770 (0.135) | 0.075 (0.142)[2] |
|  | CTG | >10 | 2.00 | 0.131 (0.015) | 0.274 (0.028) | 0.131 (0.015) | 0.059 (0.013) | 0.318 (0.021) | —[1] |
| NmuMG | calcein AM | >10 | >10 | 1.645 (0.430) | 0.553 (0.094) | 1.645 (0.430) | 0.231 (0.046)[2] | 0.671 (0.098)[2] | 0.893 (0.201)[2] |
|  | CTG | >10 | >10 | 0.630 (0.056) | 0.513 (0.107) | 0.630 (0.056) | —[1] | 0.942 (0.071) | 0.021 (0.007) |

Example 11

Tubulin Polymerization Assay

In vitro tubulin polymerization assays were performed using a fluorescence-based assay (Cytoskeleton, Inc., Denver, Colo.). Test compounds and control stocks were prepared at a final concentration of 15 μM and 3 μM in room temperature sterile ddH$_2$O. Aliquots (5 μL) of each compound or control were added to a 96-well black half area plate (Corning Costar, Inc.) pre-warmed to 37° C. Cold tubulin reaction mix (50 μL 1× Buffer-80 mM piperazine-N,N'-bis[2-ethanesulfonic acid] sequisodium salt; 2.0 mM magnesium chloride; 0.5 mM ethylene glycol-bis[β-amino-ethyl ether) N,N,N',N'-tetra-acetic acid, pH 6.9, 10 μM fluorescent reporter; 20% tubulin glycerol buffer-80 mM piperazine-N,N'-bis[2-ethanesulfonic acid] sequisodium salt; 2.0 mM magnesium chloride; 0.5 mM ethylene glycol-bis(β-amino-ethyl ether) N,N,N',N'-tetra-acetic acid, 60% v/v glycerol, pH 6.9, 1 mM GTP; and 2 mg mL$^{-1}$ tubulin stock) was added to each of the compounds. The reaction was immediately read using a 350 excitation and a 435 emission filter on a Safire microplate reader (Tecan Instruments, Mannedorf, CH), reading every sixty seconds for sixty-one cycles with temperature control set to 37° C. and shaking the plate for five seconds before the first read. Polymerization curves were generated in Excel after background correction and the effects of test compounds were compared to controls.

Library members that accelerated the rate of tubulin polymerization were deemed microtubule stabilizers, whereas compounds that decelerated the rate of tubulin polymerization were deemed microtubule de-stabilizers. Fifteen library members (6-8, Col6, Col16, Col19, Col21, Col34, Col38, Col44, Col45, Col56, Col53, Col18, Col65) were tested in duplicate on at least two separate days in the in vitro tubulin polymerization assay. Compounds 6-8, Col6, Col16, Col34, Col38, Col44, and Col45 destabilized microtubules like the parent molecule colchicine. Library members Col18, Col56 and Col65 had no effect on tubulin polymerization in this assay and two library members (Col19 and Col21) stabilized the microtubules like paclitaxel. Library member Col53 precipitated and was not further tested. The library members that had no effect (Col18, Col56 and Col65) were further tested in a wound healing assay at a sub-toxic concentration (the IC$_{10}$) and were shown to inhibit the migration of MB-MDA-231 cells by at least 50% similar to both colchicine and paclitaxel tested in the same assay.

Example 12

Wound Healing Assay

A highly metastatic and migratory human breast adenocarcinoma cell line, MB-MDA-231, was used to assess inhibition of cell migration by test compounds that did not stabilize or destabilize microtubules in the in vitro tubulin polymerization assay. Fifty thousand cells per well were plated and allowed to attach to each well of a black tissue culture treated ninety-six well microtiter plate (Corning Costar, Inc., Corning, N.Y.). Cells are grown overnight at 37° C. to allow attachment and a monolayer to form. A uniform 1.58 mm wound was created using a 96-well floating pin tool (V & P Scientific) as a guide that forms a wound along the X-axis of each well of a 96 well plate. Wounded monolayers were treated with compounds for 96 hours to allow full wound closure. Following incubation, wounded monolayers were washed 1× in phosphate buffered saline pH 7.4, and stained with Calcein AM (acetoxymethyl ester) reagent (30 μL, 1 M)

for 30 minutes at 37° C. Plates were read at excitation 485 nm and emission 535 nm in both the area of the wound and the whole well. Amount of wound healing was determined by dividing the fluorescence in the area of the wound by the total fluorescence per well. Percent inhibition was determined by dividing the amount of wound healing in treated wells by the amount of wound healing in cells treated with solvent only (DMSO).

Example 13

Multiple Drug Effect Analysis

Ten thousand A549 cells per well were plated in triplicate in 96 well black tissue culture treated plates. Cells were incubated for one hour at 37° C. to allow cells to attach. Cells were treated with different test compounds in combination with paclitaxel or colchicine. The concentration of colchicine and paclitaxel was held constant at the calculated $IC_{10}$ (concentration of compound that gives 10% growth inhibition) from the cytotoxicity assay in A549 cells. Each compound was tested in triplicate serial dilutions starting at the calculated $IC_{10}$ in combination with paclitaxel or colchicines. The combination index (CI) method of Chou and Talalay (Chou T.-C.; Hayball, M. P. Dose effect analysis; software and manual. Biosoft, Cambridge, U.K., 1996) was used to analyze the nature of the interaction between the test compounds and taxol or colchicines by determining a CI using Calcusyn software (Biosoft, Inc.) CI values of less than or greater than one indicate synergism or antagonism, respectively.

Specifically, 6-8, Col6, Col16, Col19, Col21, Col34, and Col45 were tested in combination with paclitaxel and colchicine and the synergistic effects were calculated using the Chou Talalay method (Chou T.-C.; Hayball, M. P. Dose effect analysis; software and manual. BIOSOFT, Cambridge, U.K., 1996) by determining a combination index in Calcusyn software (Biosoft, Inc.). The results are presented in Table 5 and the guide for data interpretation presented in Table 6. Library members 6, 8, Col6, and Col16 all displayed synergy with taxol (and antagonism with colchicines) similar to colchicine. In a similar fashion, library members Col21, Col34, and Col45 showed strong synergism with taxol and strong antagonism with colchicine. Library members Col19 and Col21 showed synergism with colchicine and antagonism with taxol with Col19 displaying reproducibly stronger effects. All synergy experiment results were replicated at least three times and the overall effects analyzed by averaging all combination indexes generated if the fraction affected was greater than 0.2. Col38 and Col44 were eliminated from the analysis due to impurities. Table 6 shows the recommended symbols descriptors for the combination index method used in some above studies.

TABLE 5

Drug combination studies.

| library member | plus colchicine (mean CI/median CI) | | plus paclitaxel (mean CI/median CI) | |
|---|---|---|---|---|
| taxol | 0.67 | 0.42 | N/A | N/A |
| colchicine | N/A | N/A | 0.77 | 0.18 |
| 6 | 2.32 | 1.96 | 0.57 | 0.20 |
| 7 | 3.16 | 2.20 | 0.21 | 0.09 |
| 8 | 2.98 | 1.47 | 0.90 | 0.57 |
| Col 6 | 1.30 | 1.19 | 0.88 | 0.52 |
| Col16 | 5.97 | 5.33 | 0.40 | 0.11 |
| Col19 | 0.54 | 0.50 | 43.20 | 13.40 |
| Col21 | 1.01 | 0.64 | 4.96 | 2.50 |

TABLE 5-continued

Drug combination studies.

| library member | plus colchicine (mean CI/median CI) | | plus paclitaxel (mean CI/median CI) | |
|---|---|---|---|---|
| Col34 | 31.49 | 21.50 | 0.18 | 0.12 |
| Col45 | 107.40 | 102.90 | 0.12 | 0.07 |

TABLE 6

Recommended symbol descriptors for the combination index (CI) method.

| Combination Index (CI) Range | symbol | description |
|---|---|---|
| <0.1 | +++++ | very strong synergism |
| 0.1-0.3 | ++++ | strong synergism |
| 0.3-0.7 | +++ | synergism |
| 0.7-0.85 | ++ | moderate synergism |
| 0.85-0.90 | + | slight synergism |
| 0.90-1.10 | +− | nearly additive |
| 1.10-1.20 | − | slight antagonism |
| 1.20-1.45 | −− | moderate antagonism |
| 1.45-3.3 | −−− | antagonism |
| 3.3-10 | −−−− | strong antagonism |
| >10 | −−−−− | very strong antagonism |

The above data show that the cytotoxic effect of colchicine neoglycosides in combination with other known therapeutic agents is greater than the effect of either the neoglycoside alone or the known therapeutic. These data indicate that the synergistic effect of a colchicine neoglycoside, in combination with other known therapeutics, is greater than the cytotoxic effect of either the therapeutic or the neoglycoside alone.

Disclosed herein, the inventors have shown the efficacy of methods for glycosylating natural products that naturally do not contain a carbohydrate moiety. In addition, the inventors have shown the utility of extending neoglycosylation to amine-bearing scaffolds. Further, the inventors have disclosed herein, new glycosylated analogs of colchicine that are shown to have cytotoxic properties as effective or more effective than other well-recognized drugs including, but not limited to colchine, doxorubicin and paclitaxel. These compounds represent diverse drug groups such as the alkaloids, anthracyclines and the taxanes effective not just in treating cancers but also having antibiotic and anti-inflammatory effects.

While this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:
1. A colchicine neoglycoside having the structure:
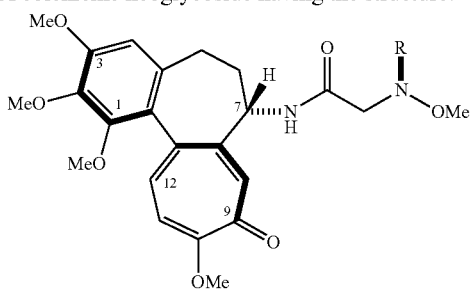
wherein R is:
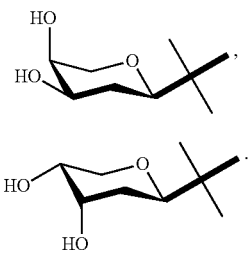
2. A method of synthesizing a colchicine neoglycoside according to the reaction:
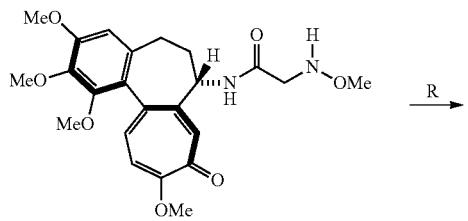
-continued
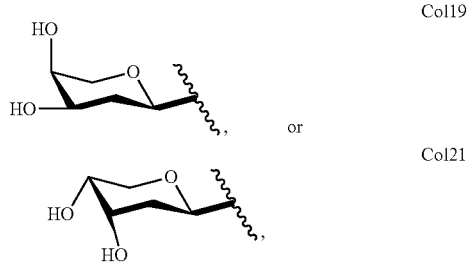
wherein R is:
Col19
HO
HO
or
Col21
HO
HO
and wherein the reaction is carried out at 40° C. in the presence of 3:1 dimethylformamide/acetic acid.
* * * * *